US006451991B1

(12) United States Patent
Martin et al.

(10) Patent No.: US 6,451,991 B1
(45) Date of Patent: *Sep. 17, 2002

(54) SUGAR-MODIFIED GAPPED OLIGONUCLEOTIDES

(75) Inventors: Pierre Martin, Rheinfelden; Karl-Heinz Altmann, Reinach, both of (CH); Phillip Dan Cook, Vista; Brett P. Monia, Carlsbad, both of CA (US)

(73) Assignees: ISIS Pharmaceuticals, Inc., Carlsbad, CA (US); Novartis AG (CH)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/802,331

(22) Filed: Feb. 11, 1997

Related U.S. Application Data

(60) Provisional application No. 60/011,620, filed on Feb. 14, 1996.

(51) Int. Cl.[7] .......................... C12Q 1/68; C07H 21/00

(52) U.S. Cl. ....................... 536/23.1; 435/6; 436/501; 536/24.5

(58) Field of Search ..................... 435/6; 436/501; 536/23.1, 24.1, 24.5, 24.3–24.33, 25.3; 935/77, 78

(56) References Cited

U.S. PATENT DOCUMENTS

| 3,687,808 A | 8/1972 | Merigan, Jr. et al. ......... 195/28 |
| 5,013,830 A | 5/1991 | Ohtsuka et al. ................ 536/27 |
| 5,149,797 A | 9/1992 | Pederson et al. ............. 536/27 |
| 5,256,775 A | 10/1993 | Froehler .................... 536/25.6 |
| 5,334,711 A | 8/1994 | Sproat et al. ............... 536/24.5 |
| 5,627,053 A | 5/1997 | Usman et al. ............... 435/91.1 |
| 5,652,355 A | 7/1997 | Metelev et al. ............. 536/24.5 |
| 5,969,116 A | 10/1999 | Martin ....................... 536/22.1 |
| 6,143,881 A | 11/2000 | Metelev et al. ............ 536/24.5 |

FOREIGN PATENT DOCUMENTS

| EP | 0339842 A2 | 11/1989 |
| EP | 0626387 A1 | 11/1994 |
| WO | WO 92/03568 | 3/1992 |
| WO | WO 92/22651 | 12/1992 |
| WO | WO 94/02501 | 2/1994 |

OTHER PUBLICATIONS

Iribarren et al., Proceedings of the National Acad. of Sci (USA), vol. 87, pp. 7747–7751, 1990.*

Stein, C.A., et al., "Antisense oligonucleotides as therapeutic agents—is the bullet really magical?," Science, Aug. 20, 1993, 261, 1004–1012.

Acevedo et al., Synthesis and Biophysical Evaluation of antisense oligonucleotides containing 3–deaza–3–substituted guanines, Conferernce on Nucleic Acid Therapeutics, Clearwater, FL, Jan. 13, 1991.

Borer et al., "Stability of Ribonucleic Acid Double–stranded Helics", J. Mol. Bio., 1974, 86, 843–853.

Dagle et al., "Targeted degradation of mRNA in Xenopus oocytes and embryos directed by modified oligonucleotides: studies of An2 and Cyclin in embryogenesis", Nucl. Acids Res., 1990, 18(16), 4751–4757.

Dagle et al., "Physical properties of oligonucleotides containing phosphoramidate–modified internucleoside linkages", Nucl. Acids Res., 1991, 19(8), 1805–1810.

Dagle et al., "Pathways of Degradation and Mechanism of Action of Antisense Oligonucleotides in Xenopus laevis Embryos", Antisense Res. Develop., 1991, 1, 11–20.

Dignam et al., "Accurate transcriptioin initiation by RNA polymerase II in a soluble extract from isolated mammalian nuclei", Nucl. Acids Res., 1983, 11(5), 1475–1489.

Eder et al., "Ribonuclease H from K562 Human Erythroleukemia Cells", J. Biol. Chem., 1991, 266 (10), 6472–6479.

Englisch et al., "Chemically Modified Oligonucleotides as Probes and Inhibitors", Angewandte Chemie, Int'l Ed., 1991, 30(6), 613–629.

Graham et al., "Tritium labeling of antisense oligonucleotides by exchange with tritiated water", Nucl. Acids Res., 1993, 21 (16), 3737–3743.

Kroschwitz, J. I. (ed.), Concise Encyclopedia of Polymer Science and Engineering, John Wily & Sons, 1990, 858–859.

Martin, "A New Access to 2'–O–Alkylated Ribonucleosides and Properties of 2'–O–Alkylated Oligoribonucleotides", Helv. Chim. Acta, 1995, 78, 486–504.

Owen et al., "Transcriptional activation of a conserved sequence element by ras requires a nuclear factor distinct from c–fos or c–jun", Proc. Natl. Acad. Sci. USA, 1990, 87, 3866–3870.

Petersheim et al., "Base–Stacking and Base–Pairing Contribtions to Helix Stability: Thermodynamics of Double–Helix Formation with CCGG, CCGGp, CCGGAp, ACCGGp, CCGGUp, and ACCGGUp", Biochem., 1983, 22, 256–263.

Puglishi et al., "Absorbance Melting Curves of RNA", Methods in Enzymol., 1989, 180, 304–325.

(List continued on next page.)

Primary Examiner—Ardin H. Marschel
(74) Attorney, Agent, or Firm—Woodcock Washburn, LLP

(57) ABSTRACT

Oligonucleotides are provided which have increased nuclease resistance, substituent groups for increasing binding affinity to complementary nucleic acid strand, and subsequences of 2'-deoxy-erythro-pentofuranosyl nucleosides that activate RNase H. Such oligonucleotides are useful for diagnostics and other research purposes, for modulating the expression of a protein in organisms, and for the diagnosis, detection and treatment of other conditions susceptible to ooligonucleotide therapeutics.

14 Claims, 15 Drawing Sheets

OTHER PUBLICATIONS

Saison–Behmoaras et al., "Short modified antisense oligonucleotdies directed against Ha–ras point mutation induce selective cleavage of the mRNA and inhibit T24 cells proliferation", *EMBO J.*, 1991, 10 (5), 1111–1118.

Sambrook et al., "Molecular Cloning. A Laboratory Manual", Cold Spring Harbor Laboratory Press, 1989, vol. 2, 11.31–11.32.

Schwartz et al., "A microtransfection method using the luiferase–encoding reporter gene for the assay of human immuno–deficiency virus LTR promoter activity", *Gene*, 1990, 88, 197–205.

Stein et al., "Antisense Oligonucleotides as Therapeutic Agents—Is the Bullet Really magic?", *Science*, 1993, 261, 1004–1012.

McKay, R.A. et al., "Enhanced activity of an antisense oligonucleotide targeting murine protein kinase Cβ by the incorporation of 2'–O–propyl modifications", *Nucl. Acids Res.*, 1996, 24(3), 411–417.

Monia, B.P. et al., "Nuclease Resistance and Antisense Activity of Modified Oligonucleotides Targeted to HA–ras", *J. Biol. Chem.*, 1996, 271(24), 14533–14540.

Monia, B.P. et al., "Evaluation of 2'–Modified Oligonucleotides Containing 2'–Deoxy Gaps as Antisense Inhibitors of Gene Expression", *J. Biol. Chem.*, 1993, 268(19), 14514–14522.

\* cited by examiner

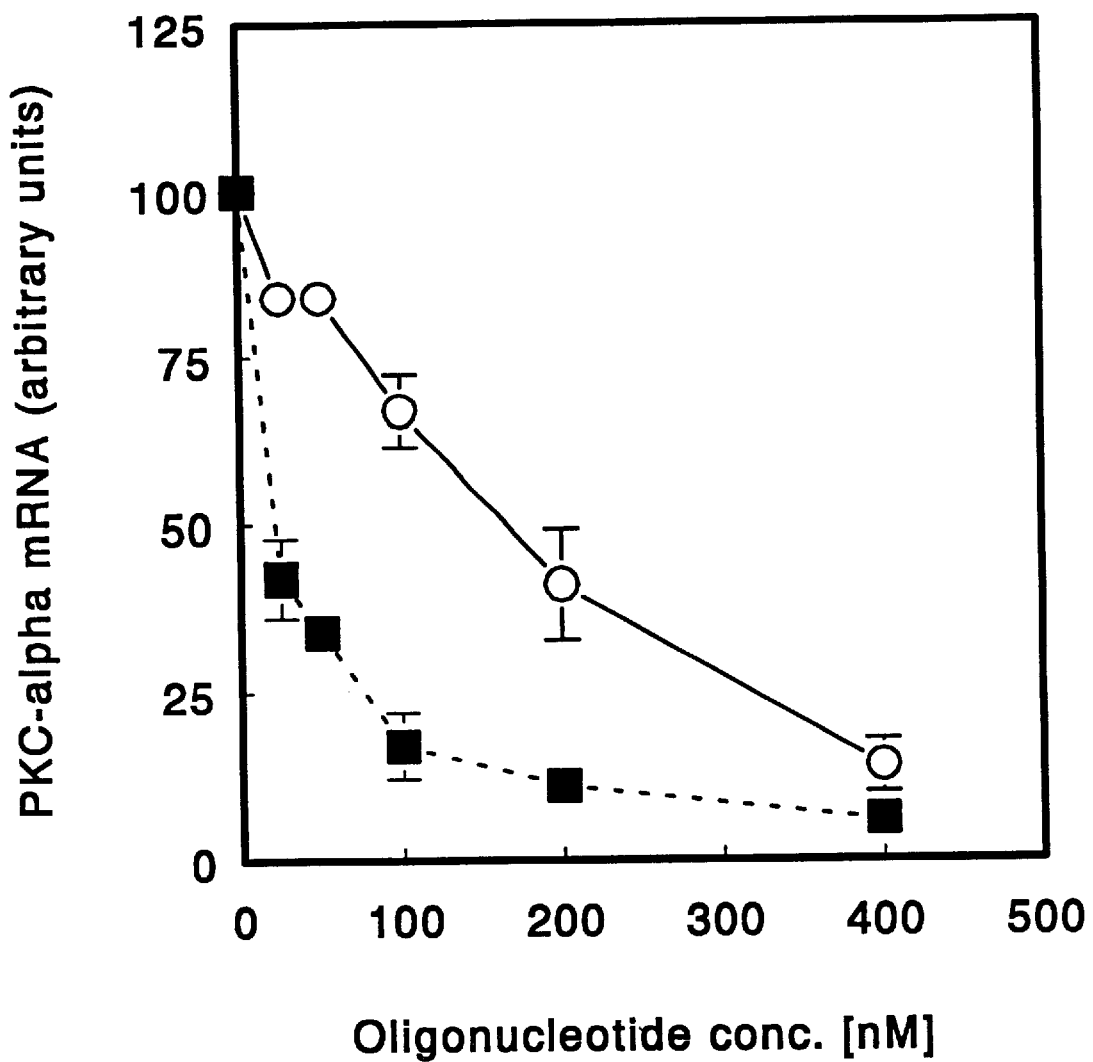

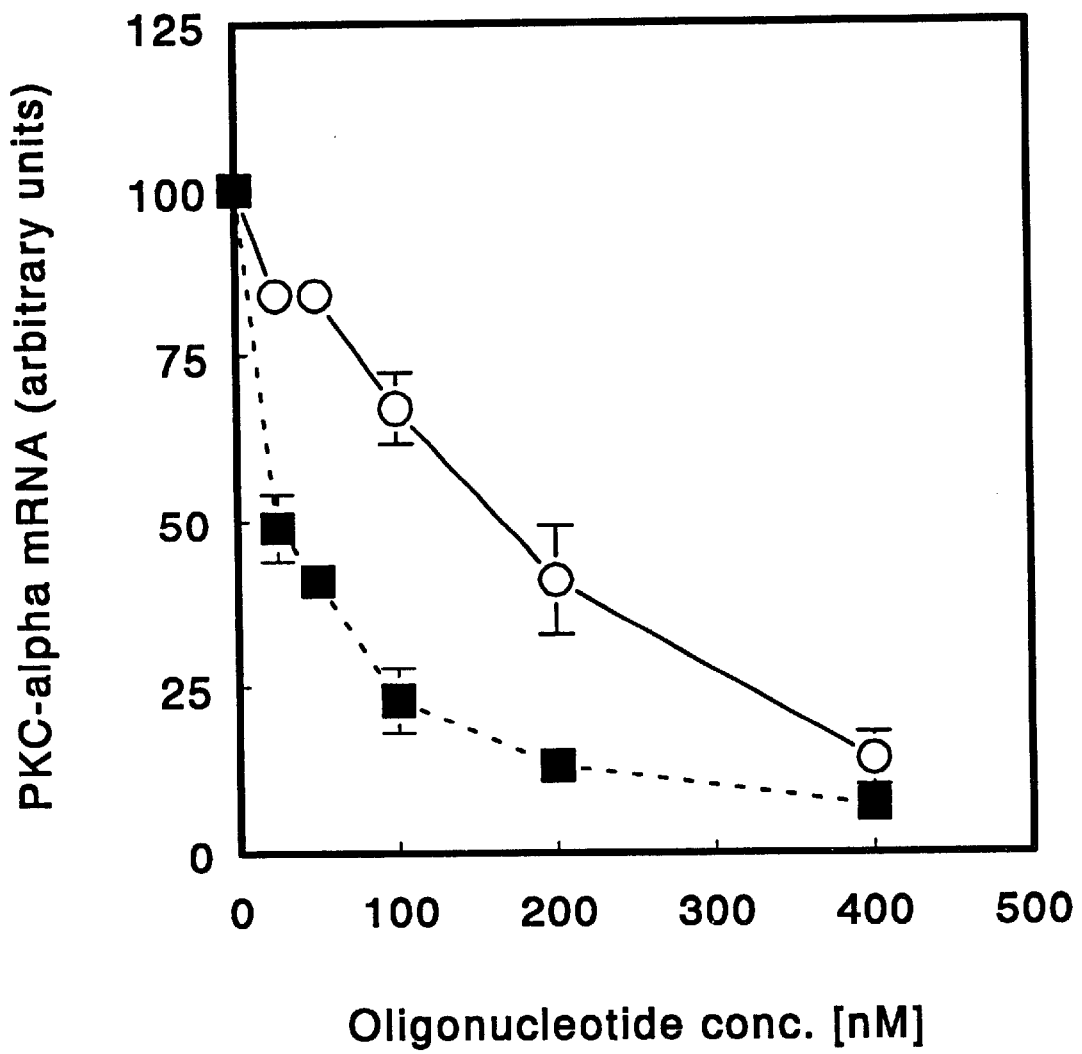

SUGAR-MODIFIED GAPPED OLIGONUCLEOTIDES

CROSS-REFERENCE TO RELATED APPLICATION

This application claims the benefit of U.S. Provisional Application Ser. No. 60/011620, filed Feb. 14, 1996.

FIELD OF THE INVENTION

This invention is directed to the synthesis and use of oligonucleotides for eliciting RNase H activity for strand cleavage in an opposing strand. Included in the invention are oligonucleotides wherein at least some of the nucleoside units of the oligonucleotides are functionalized to be nuclease resistant, at least some of the nucleoside units of the oligonucleotides include a substituent that potentiates hybridization of the oligonucleotide to a complementary strand of nucleic acid, and at least some of the nucleoside units of the oligonucleotides include 2'-deoxy-erythro-pentofuranosyl sugar moieties. The oligonucleotides are useful for therapeutics, diagnostics and as research reagents.

BACKGROUND OF THE INVENTION

Oligonucleotides are known to hybridize to single-stranded DNA or RNA molecules. Hybridization is the sequence-specific base pair hydrogen bonding of nucleobases of the oligonucleotides to nucleobases of target DNA or RNA. Such nucleobase pairs are said to be complementary to one another.

In determining the extent of hybridization of an oligonucleotide to a complementary nucleic acid, the relative ability of an oligonucleotide to bind to the complementary nucleic acid may be compared by determining the melting temperature of a particular hybridization complex. The melting temperature ($T_m$), a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking which occurs during hybridization, is accompanied by a reduction in UV absorption (hypochromicity). Consequently, a reduction in UV absorption indicates a higher $T_m$. The higher the $T_m$, the greater the strength of the bonds between the strands.

Oligonucleotides can be used to effect enzymatic cleavage of a target RNA by using the intracellular enzyme, RNase H. The mechanism of such RNase H cleavage is believed to require that a 2'-deoxyribofuranosyl oligonucleotide hybridize to a target RNA. The resulting DNA-RNA duplex activates the RNase H enzyme and the activated enzyme cleaves the RNA strand. Cleavage of the RNA strand destroys the normal function of the RNA. Phosphorothioate oligonucleotides are believed to operate via this type of mechanism. However, for a DNA oligonucleotide to be useful for cellular activation of RNase H, the oligonucleotide preferably is reasonably stable to nucleases in order to survive in cells for a time period sufficient for RNase H activation. For non-cellular uses, such as use of oligonucleotides as research reagents, such nuclease stability may not be necessary.

Several publications describe the interaction of RNase H and oligonucleotides. Of particular interest are: (1) Dagle et al., *Nucleic Acids Research*, 1990, 18, 4751; (2) Dagle et al., *Antisense Research And Development*, 1991, 1, 11; (3) Eder et al., *J. Biol. Chem.*, 1991, 266, 6472; and (4) Dagle et al., *Nucleic Acids Research*, 1991, 19, 1805. According to these publications, DNA oligonucleotides having both unmodified phosphodiester internucleoside linkages and modified phosphorothioate internucleoside linkages are substrates for cellular RNase H. Since they are substrates, they activate the cleavage of target RNA by RNase H. However, the authors further noted that in Xenopus embryos, both phosphodiester linkages and phosphorothioate linkages are also subject to exonuclease degradation. Such nuclease degradation is detrimental since it rapidly depletes the oligonucleotide available for RNase H activation.

As described in references (1), (2) and (4), to stabilize oligonucleotides against nuclease degradation while still providing for RNase H activation, 2'-deoxy oligonucleotides having a short section of phosphodiester linked nucleosides positioned between sections of phosphoramidate, alkyl phosphonate or phosphotriester linkages were constructed. While the phosphoramidate-containing oligonucleotides were stabilized against exonucleases, in reference (4) the authors noted that each phosphoramidate linkage resulted in a loss of 1.6° C. in the measured $T_m$ value of the phosphoramidate-containing oligonucleotides. Such a decrease in the $T_m$ value is indicative of a decrease in hybridization between the oligonucleotide and its target strand.

Other authors have commented on the effect such a loss of hybridization between an oligonucleotide and its target strand can have. Saison-Behmoaras et al. (*EMBO Journal*, 1991, 10, 1111) observed that even though an oligonucleotide could be a substrate for RNase H, cleavage efficiency by RNase H was low because of weak hybridization to the mRNA. The authors also noted that the inclusion of an acridine substitution at the 3' end of the oligonucleotide protected the oligonucleotide from exonucleases.

U.S. Pat. No. 5,013,830, issued May 7, 1991, discloses mixed oligomers comprising an RNA oligomer, or a derivative thereof, conjugated to a DNA oligomer via a phosphodiester linkage. The RNA oligomers also bear 2'-O-alkyl substituents. However, being phosphodiesters, the oligomers are susceptible to nuclease cleavage.

European Patent application 339,842, filed Apr. 13, 1989, discloses 2'-O-substituted phosphorothioate oligonucleotides, including 2'-O-methylribooligonucleotide phosphorothioate derivatives. The above-mentioned application also discloses 2'-O-methyl phosphodiester oligonucleotides which lack nuclease resistance.

U.S. Pat. No. 5,149,797, issued Sep. 22, 1992, discloses mixed phosphate backbone oligonucleotides which include an internal portion of deoxynucleotides linked by phosphodiester linkages, and flanked on each side by a portion of modified DNA or RNA sequences. The flanking sequences include methyl phosphonate, phosphoromorpholidate, phosphoropiperazidate or phosphoramidate linkages.

U.S. Pat. No. 5,256,775, issued Oct. 26, 1993, describes mixed oligonucleotides that incorporate phosphoramidate linkages and phosphorothioate or phosphorodithioate linkages.

While it has been recognized that cleavage of a target RNA strand using an oligonucleotide and RNase H would be useful, nuclease resistance of the oligonucleotide and fidelity of hybridization are of great importance in the development of oligonucleotide therapeutics. Accordingly, there remains a long-felt need for methods and materials that could activate RNase H while concurrently maintaining or improving hybridization properties and providing nuclease resistance. Such oligonucleotides are also desired as research reagents and diagnostic agents.

SUMMARY OF THE INVENTION

In accordance with one embodiment of this invention there are provided oligonucleotides formed from a sequence of nucleoside units. The oligonucleotides incorporate a least one nucleoside unit that is functionalized to increase nuclease resistance of the oligonucleotides. Further, at least some of the nucleoside units of the oligonucleotides are functionalized with a substituent group to increase binding affinity of the oligonucleotides for target RNAs, and at least some of the nucleoside units have 2'-deoxy-erythro-pentofuranosyl sugar moieties.

In preferred oligonucleotides of the present invention, nucleoside units which are functionalized for increasing binding affinity include a 2'-substituent group. In preferred embodiments, the 2'-substituent group includes fluoro, $C_1$–$C_{20}$ alkoxy, $C_1$–$C_9$ aminoalkoxy, including aminopropoxy, allyloxy, imidazolylalkoxy and polyethylene glycol. Preferred alkoxy substituents include methoxy, ethoxy and propoxy. A preferred aminoalkoxy unit is aminopropoxy. A preferred imidazolylalkoxy substituent is imidazolylpropoxy. A preferred polyethylene glycol substituent is —O-ethyl-O-methyl or methoxyethoxy (—O—$CH_2$—$CH_2$—O—$CH_3$).

The oligonucleotides of the present invention include nucleoside units connected by charged phosphorus linkages selected from a group consisting of phosphodiester and phosphorothioate linkages.

The oligonucleotides of the present invention include a plurality of linked nucleoside units bearing substituent groups that increase binding affinity of the oligonucleotide to a complementary strand of nucleic acid. In certain preferred embodiments, the sequence of an oligonucleotide having nucleoside units that bear such substituents can be divided into a first subsequence and a second subsequence, with the first subsequence having linked nucleoside units bearing 2'-substituted-erythro-pentofuranosyl sugar moieties and the second subsequence having linked nucleoside units bearing 2'-deoxy-erythro-pentofuranosyl sugar moieties. Preferably, said second subsequence has at least three nucleoside units, and more preferably, has at least five nucleoside units. In further preferred embodiments there exists a third subsequence, the nucleoside units of which are selected from those which are selectable for the first subsequence. It is preferred that the second subsequence be positioned between the first and the third subsequences. Such oligonucleotides of the present invention are also referred to as "chimeras," or "chimeric" or "gapped" oligonucleotides.

In further preferred oligonucleotides of the invention, nucleoside units bearing substituents that increase binding affinity are located at one or both of the 3' or the 5' termini of the oligonucleotide. There can be from one to about eight nucleoside units that are substituted with substituent groups. Preferably, at least five nucleoside units bear 2'-deoxy-erythro-pentofuranosyl sugar moieties.

The nucleoside units of the oligonucleotides of the present invention comprise nucleobases linked to 2'-substituted and 2'-deoxy-erythro-pentofuranosyl sugar moieties by phosphorus linkages such as phosphodiester and phosphorothioate linkages. Preferred nucleobases of the invention include purines and pyrimidines such as adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 8-halo, amino, thiol, thioalkyl, hydroxyl and other 8-substituted adenines and guanines, 5-trifluoromethyl and other 5-substituted uracils and cytosines, and 7-methylguanine. Further purines and pyrimidines include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, and those disclosed by Englisch et al., *Angewandte Chemie, International Edition*, 1991, 30, 613.

The invention also provides methods for treating an organism having a disease characterized by the undesired production of a protein. These methods include contacting the organism with an oligonucleotide having a sequence of nucleoside units capable of specifically hybridizing with a complementary strand of nucleic acid with at least one of the nucleoside units being functionalized to increase nuclease resistance of the oligonucleotide to nucleases, with a substituent group located thereon to increase binding affinity of the oligonucleotide to the complementary strand of nucleic acid, and with a plurality of the nucleoside units having 2'-deoxy-erythro-pentofuranosyl sugar moieties.

Further in accordance with the present invention there are provided compositions including a pharmaceutically effective amount of an oligonucleotide having a sequence of nucleoside units capable of specifically hybridizing with a complementary strand of nucleic acid having at least one of the nucleoside units functionalized to increase nuclease resistance of the oligonucleotide to nucleases, wherein a plurality of the nucleoside units have a substituent group located thereon to increase binding affinity of the oligonucleotide to the complementary strand of nucleic acid, and wherein a plurality of the nucleoside units have 2'-deoxy-erythro-pentofuranosyl sugar moieties. The compositions further include a pharmaceutically acceptable diluent or carrier.

Further in accordance with this invention there are provided methods for in vitro modification of a sequence-specific nucleic acid including contacting a test solution containing an RNase H enzyme and said nucleic acid with an oligonucleotide having a sequence of nucleoside units capable of specifically hybridizing to a complementary strand of the nucleic acid, where at least one of the nucleoside units is functionalized to increase nuclease resistance of the oligonucleotide to nucleases, where a plurality of the nucleoside units have a substituent group located thereon to increase binding affinity of the oligonucleotide to the complementary strand of nucleic acid, and where a plurality of the nucleoside units have 2'-deoxy-erythro-pentofuranosyl sugar moieties.

There are also provided methods of concurrently enhancing hybridization and RNase H enzyme activation in an organism that includes contacting the organism with an oligonucleotide having a sequence of nucleoside units capable of specifically hybridizing to a complementary strand of nucleic acid, where at least one of the nucleoside units is functionalized to increase nuclease resistance of the oligonucleotide to nucleases, where a plurality of the nucleoside units have a substituent group located thereon to increase binding affinity of the oligonucleotide to the complementary strand of nucleic acid, and where a plurality of the nucleoside units have 2'-deoxy-erythro-pentofuranosyl sugar moieties.

The invention further provides diagnostic methods for detecting the presence or absence of abnormal RNA molecules, or abnormal or inappropriate expression of normal RNA molecules in organisms or cells.

BRIEF DESCRIPTION OF THE DRAWINGS

FIGS. 6a and 6b are line graphs showing the effect of 2' methoxyethoxy modified oligonucleotides having SEQ ID NO: 30 on PKCα mRNA levels in A549 cells. FIG. 6a shows the effect of ISIS 9605 compared to the deoxyphosphorothioate compound, ISIS 3521. FIG. 6b shows the effect of ISIS 9606 compared to the deoxyphosphorothioate compound, ISIS 3521.

FIG. 7a shows the effect of the deoxyphosphorothioate compound, ISIS 3521. FIG. 7b shows the effect of the 2' methoxyethoxy modified compound, ISIS 12723.

DETAILED DESCRIPTION OF THE INVENTION

Figure 1:
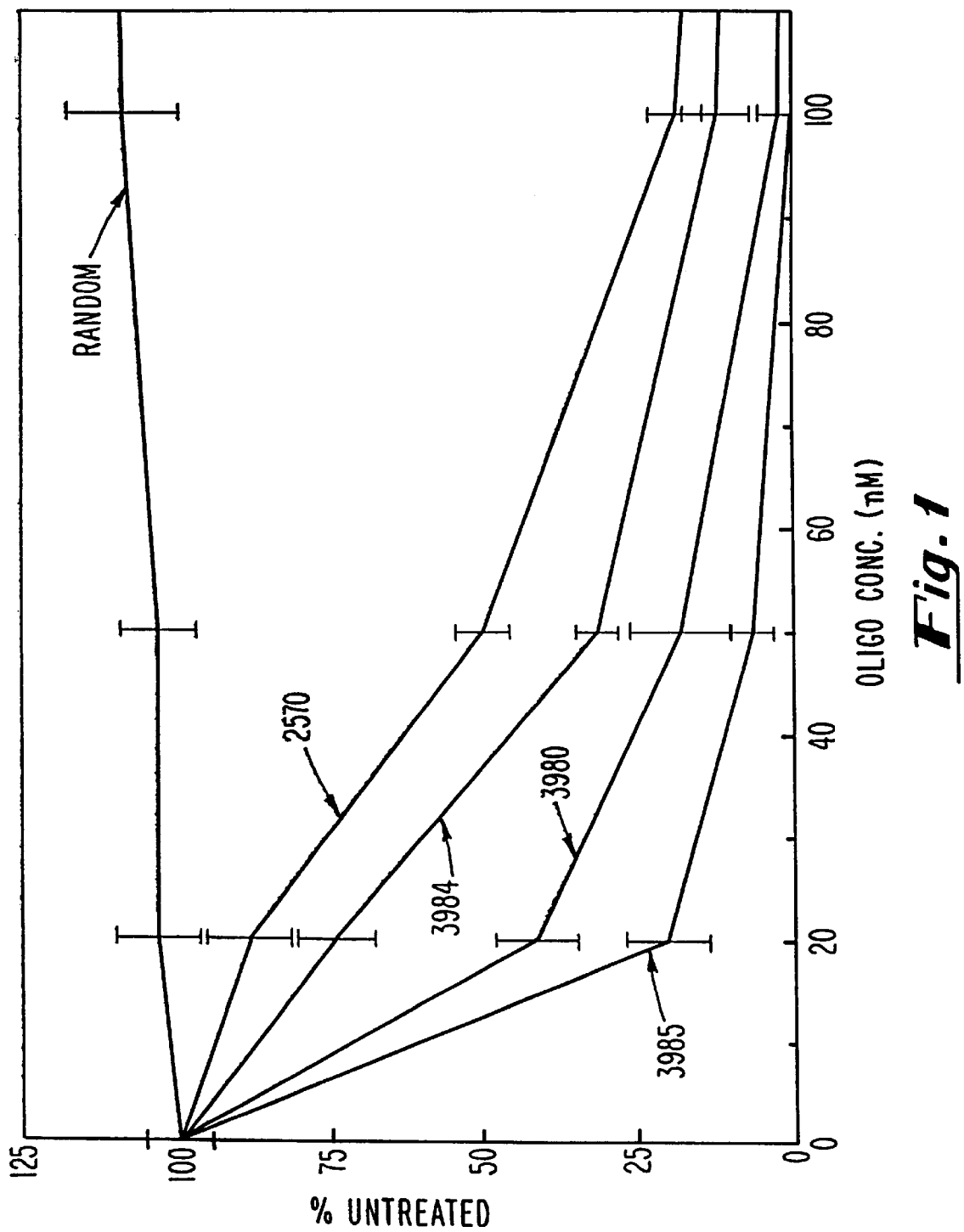
FIG. 1 is a line graph showing dose response activity of oligonucleotides of the invention and a reference compound.

In accordance with the objects of this invention, novel oligonucleotides which have increased nuclease resistance, increased binding affinity to complementary strands of nucleic acids and that are substrates for RNase H are provided; The oligonucleotides of the invention are assembled from a plurality of nucleoside units. Each oligonucleotide of the invention includes at least one nucleoside unit that is functionalized to increase the nuclease resistance of the oligonucleotide. Further, in certain embodiments of the invention, at least some of the nucleoside units bear a substituent group that increases the binding affinity of the oligonucleotide for a complementary strand of nucleic acid. Additionally, at least some of the nucleoside units comprise 2'-deoxy-erythro-pentofuranosyl sugar moieties.

In conjunction with the above guidelines, each nucleoside unit of an oligonucleotide of the invention, alternatively referred to as a "nucleoside" or "subunit," can be a "natural" or "synthetic" moiety. Thus, in the context of this invention, the term "oligonucleotide" refers to an oligomer formed from a plurality of joined nucleoside units. The nucleoside units are joined together via phosphorus linkages such as phosphodiester or phosphorothioate linkages. The nucleoside units are formed from naturally or non-naturally occurring nucleobases and pentofuranosyl sugar moieties. The term "oligonucleotide" thus effectively includes naturally occurring species or synthetic species formed from naturally occurring nucleoside units.

Oligonucleotides of the invention can also include modified subunits. The modifications can occur on the nucleobase portion of a nucleoside, on the sugar portion of a nucleoside or on the linkage joining one nucleoside to the next.

It is found in the present invention that the binding affinity of oligonucleotides of the present invention can be increased by incorporating substituent groups in the nucleoside units of the oligonucleotides. Preferred substituent groups are 2' substituent groups, i.e. substituent groups located at the 2' position of the pentofuranosyl sugar moieties of the nucleoside units of the oligonucleotides of the present invention. Presently preferred substituent groups include fluoro, alkoxy, aminoalkoxy, allyloxy, imidazolylalkoxy and polyethylene glycol. Alkoxy and aminoalkoxy groups generally include lower alkyl groups, particularly $C_1$–$C_9$ alkyl. Polyethylene glycols are of the structure (O—CH$_2$—CH$_2$)$_n$—O-alkyl. A particularly preferred substituent group is a polyethylene glycol substituent of the formula (—O—CH$_2$—CH$_2$)$_n$—O-alkyl, wherein n=1 and alkyl=CH$_3$.

Binding affinity can also be increased by the use of certain modified nucleobases in the nucleoside units that make up the oligonucleotides of the invention. Such modified nucleobases may include 5-substituted pyrimidines, 6-azapyrimidines and N-2, N-6 and O-6 substituted purines, including 2-aminopropyladenine, 5-propynyluracil and 5-propynylcytosine. Other modified pyrimidine and purine bases are expected to increase the binding affinity of oligonucleotides to a complementary strand of nucleic acid.

The use of 2'-substituent groups increases the binding affinity of the substituted oligonucleotides of the present invention. A published study (Synthesis and Biophysical Studies of 2'-dRIBO-F Modified Oligonucleotides, Conference On Nucleic Acid Therapeutics, Clearwater, Fla., Jan. 13, 1991), has reported an increase in binding affinity of 1.6° C. per substituted nucleoside unit of a 15-mer phosphodiester oligonucleotide having 2'-fluoro substituent groups on five of the nucleoside units of the oligonucleotide. When 11 of the nucleoside units of the oligonucleotide bore 2'-fluoro substituent groups, the binding affinity increased to 1.8° C. per substituted nucleoside unit.

In the above-mentioned study, the 15-mer phosphodiester oligonucleotide was derivatized to the corresponding phosphorothioate analog. When the 15-mer phosphodiester oligonucleotide was compared to its phosphorothioate analog, the phosphorothioate analog had a binding affinity of only about 66% of that of the 15-mer phosphodiester oligonucleotide. Stated otherwise, binding affinity was lost in derivatizing the oligonucleotide to its phosphorothioate analog. However, when 2'-fluoro substituents were located on 11 of the nucleosides of the 15-mer phosphorothioate oligonucleotide, the binding affinity of the 2'-substituent groups more than overcame the decrease noted by derivatizing the 15-mer oligonucleotide to its phosphorothioate analog. In this compound, i.e. the 15-mer phosphorothioate oligonucleotide having 11 nucleoside units substituted with 2'-fluoro substituent groups, the binding affinity was increased to 2.5° C. per substituent group. In this study no attempt was made to include an appropriate consecutive sequence of nucleoside units having 2'-deoxy-erythro-pentofuranosyl sugar moieties that would elicit RNase H enzymatic cleavage of a RNA target complementary to the oligonucleotide of the study.

In order to elicit RNase H enzymatic cleavage of a target RNA, an oligonucleotide of the invention must include a segment or subsequence therein that is a DNA-type segment. Stated otherwise, at least some of the nucleoside subunits of the oligonucleotides of the invention must have 2'-deoxy-erythro-pentofuranosyl sugar moieties. A subsequence having more than three consecutively linked 2'-deoxy-erythro-pento-furanosyl-containing nucleoside subunits is necessary in order to elicit RNase H activity upon hybridization with an oligonucleotide of the invention with a target RNA. It is presently preferred to have a subsequence of three or more consecutive 2'-deoxy-erythro-pentofuranosyl containing nucleoside subunits in an oligonucleotide of the invention. Use of at least five consecutive 2'-deoxy-erythro-pentofuranosyl-containing nucleoside subunits is particularly preferred.

The mechanism of action of RNase H is recognition of a DNA-RNA duplex followed by cleavage of the RNA stand of this duplex. As noted in the "Background of the Invention" section above, others in the art have used modified DNA strands to impart nuclease stability to the DNA strand. To do this they have used modified phosphorus linkages which impart increased nuclease stability but detract from the hybridization properties.

The present invention identifies certain criteria which must be met for RNase H to recognize and elicit cleavage of an RNA strand. The first of these is that the RNA strand at the cleavage site must have its nucleoside units connected via a phosphorus linkage that bears a negative charge. Additionally, the sugar moiety of the nucleosides at the cleavage site must be a β-pentofuranosyl sugar moiety and must also be in a 2' endo conformation. The only nucleosides that fit this criteria are 2'-deoxy-erythro-pentofuranosyl β-nucleosides connected by phosphodiester, phosphorothioate and phosphorodithioate linkages.

For use in preparing such structural units, suitable nucleobases include purines and pyrimidines such as adenine, guanine, cytosine, uridine, and thymine, as well as other synthetic and natural nucleobases such as xanthine, hypoxanthine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 8-halo, amino, thiol, thioalkyl, hydroxyl and other 8-substituted adenines and guanines, 5-trifluoromethyl and other 5-substituted uracils and cytosines, 7-methylguanine. Further purines and pyrimidines include those disclosed in U.S. Pat. No. 3,687,808, those disclosed in the *Concise Encyclopedia Of Polymer Science And Engineering,* pages 858–859, Kroschwitz, J. I., ed. John Wiley & Sons, 1990, and those disclosed by Englisch et al., *Angewandte Chemie, International Edition,* 1991, 30, 613.

The oligonucleotides of the present invention contain a methoxyethoxy ($-OCH_2CH_2OCH_3$) modification at the 2' position of at least one nucleoside. This modification has been shown to increase both affinity of the oligonucleotide for its target and nuclease resistance of the oligonucleotide. Oligonucleotides in accordance with this invention preferably comprise from about 5 to about 50 nucleoside units. In the context of this invention it is understood that this encompasses non-naturally occurring oligomers as hereinbefore described, having 5 to 50 nucleoside units. It is more preferred that the oligonucleotides of the present invention comprise from about 15 to about 25 nucleoside units. As will be appreciated, a "nucleoside unit" is a nucleobase and sugar combination suitably bound to adjacent subunits through phosphorus linkages. The term "subunit" is used interchangeably with the term "nucleoside unit." In order to elicit an RNase H response, as specified above, within this total overall sequence length of the oligonucleotide will be a subsequence of greater than three, but preferably five or more, consecutively linked 2'-deoxy-erythro-pentofuranosyl-containing nucleoside units.

It is presently preferred to incorporate the 2'-deoxy-erythro-pentofuranosyl-containing nucleoside subsequence in the oligonucleotide such that within the oligonucleotide other 2'-substituted pentofuranosyl-containing nucleoside subsequences are located on either side of the 2'-deoxy-erythro-pentofuranosyl-containing nucleoside subsequence. In such a construction, the 2'-deoxy-erythro-pentofuranosyl-containing nucleoside subsequence is also referred to as the "central region" and the 2'-substituted pentofuranosyl-containing nucleoside subsequences are referred to as "flanking regions."

In certain embodiments of the invention, if the remainder of the nucleoside units each include a 2'-substituent group for increased binding affinity, then the 2'-deoxy-erythro-pentofuranosyl-containing nucleoside subsequence will be located between a first subsequence of nucleoside units having 2'-substituent groups and a second subsequence of nucleoside units having 2'-substituent groups. Other constructions are also possible, including locating the 2'-deoxy-erythro-pentofuranosyl-containing nucleoside subsequence at either the 3' or the 5' terminus of the oligonucleotides of the present invention.

The oligonucleotides used in accordance with this invention may be conveniently and routinely made through the well-known technique of solid phase synthesis. [Martin, *Helv. Chim. Acta,* 1995, 78, 486–504.] Equipment for such synthesis is sold by several vendors including Applied Biosystems. Any other means for such synthesis may also be employed. The actual synthesis of the oligonucleotides is well within the talents of those skilled in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralin-modified amidites and/or CPG (available from Glen Research, Sterling, Va.) to synthesize fluorescently labeled, biotin or other conjugated oligonucleotides.

Compounds of the invention can be utilized as diagnostics, therapeutics and as research reagents and kits.

They can be utilized in pharmaceutical compositions by adding an effective amount of an oligonucleotide of the invention to a suitable pharmaceutically acceptable diluent or carrier. They further can be used for treating organisms having a disease characterized by the undesired production of a protein. The organism can be contacted with an oligonucleotide of the invention having a sequence that is capable of specifically hybridizing with a strand of target nucleic acid that codes for the undesirable protein.

The formulation of therapeutic compositions and their subsequent administration is believed to be within the skill of those in the art. In general, for therapeutics, a patient in need of such therapy is administered an oligonucleotide in accordance with the invention, commonly in a pharmaceutically acceptable carrier, in doses ranging from 0.01 µg to 100 g per kg of body weight depending on the age of the patient and the severity of the disease state being treated. Further, the treatment regimen may last for a period of time which will vary depending upon the nature of the particular disease, its severity and the overall condition of the patient, and may extend from once daily to once every 20 years. Following treatment, the patient is monitored for changes in his/her condition and for alleviation of the symptoms of the disease state. The dosage of the oligonucleotide may either be increased in the event the patient does not respond significantly. to current dosage levels, or the dose may be decreased if an alleviation of the symptoms of the disease state is observed, or if the disease state has been ablated.

In some cases it may be more effective to treat a patient with an oligonucieotide of the invention in conjunction with other traditional therapeutic modalities. For example, a patient being treated for AIDS may be administered an oligonucleotide in conjunction with AZT, or a patient with atherosclerosis may be treated with an oligonucleotide of the invention following angioplasty to prevent reocclusion of the treated arteries.

Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to 20 years.

Such therapeutic treatment can be practiced in a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular machinery is susceptible to such therapeutic and/or prophylactic treatment. Seemingly diverse organisms such as bacteria, yeast, protozoa, algae, plant and higher animal forms, including warm-blooded animals, can be treated in this manner. Further, since each of the cells of multicellular eukaryotes also includes both DNA-RNA transcription and RNA-protein translation as an integral part of their cellular activity, such therapeutics and/or diagnostics can also be practiced on such cellular populations. Furthermore, many of the organelles, e.g. mitochondria and chloroplasts, of eukaryotic cells also include transcription and translation mechanisms. As such, single cells, cellular populations or organelles also can be included within the definition of organisms that are capable of being treated with the therapeutic or diagnostic oligonucleotides of the invention. As used herein, therapeutics is meant to include eradication of a disease state, killing of an organism, e.g. bacterial, protozoan or other infection, or control of aberrant or undesirable cellular growth or expression.

In the context of this invention, "hybridization" shall mean hydrogen bonding, which may be Watson-Crick, Hoogsteen or reversed Hoogsteen hydrogen bonding, between complementary nucleobases. For example, adenine and thymine are complementary nucleobases which pair through the formation of hydrogen bonds. "Complementary" and "specifically hybridizable," as used herein, refer to sequence complementarity between two nucleic acids containing nucleoside units, one nucleic acid being an oligonucleotide and the other nucleic acid being a target DNA or RNA molecule. For example, if a nucleobase at a certain position of an oligonucleotide is capable of hydrogen bonding with a nucleobase at the same position of a DNA or RNA molecule, then the oligonucleotide and the DNA or RNA molecule are considered to be complementary to each other at that position. The oligonucleotide and the DNA or RNA molecule are complementary to each other when a sufficient number of corresponding positions in each molecule are occupied by nucleobases which can hydrogen bond with each other. Thus, "specifically hybridizable" and "complementary" are terms which are used to indicate a sufficient degree of complementarity such that stable and specific binding occurs between the oligonucleotide and the target DNA or RNA molecule. It is understood that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA to cause a loss of utility, and there is a sufficient degree of complementarity to avoid non-specific binding of the oligonucleotide to non-target sequences under conditions in which specific binding is desired, i.e. under physiological conditions in the case of in vivo assays or therapeutic treatment, or in the case of in vitro assays, under conditions in which the assays are performed.

For the purpose of illustration, the compounds of the invention have been used in a ras-luciferase fusion system using ras-luciferase transactivation. As described in International Publication Number WO 92/22651, published Dec. 23, 1992 and commonly assigned with this application, the entire contents of which are herein incorporated by reference, the ras oncogenes are members of a gene family that encode related proteins that are localized to the inner face of the plasma membrane. Ras proteins have been shown to be highly conserved at the amino acid level, to bind GTP with high affinity and specificity, and to possess GTPase activity. Although the cellular function of ras gene products is unknown, their biochemical properties, along with their significant sequence homology with a class of signal-transducing proteins, known as GTP binding proteins, or G proteins, suggest that ras gene products play a fundamental role in basic cellular regulatory functions related to the transduction of extracellular signals across plasma membranes.

Three ras genes, designated H-ras, K-ras, and N-ras, have been identified in the mammalian genome. Mammalian ras genes acquire transformation-inducing properties by single point mutations within their coding sequences. Mutations in naturally occurring ras oncogenes have been localized to codons 12, 13, and 61. The most commonly detected activating ras mutation found in human tumors is in codon-12 of the H-ras gene in which a base change from GGC to GTC results in a glycine-to-valine substitution in the GTPase regulatory domain of the ras protein product. This single amino acid change is thought to abolish normal control of ras protein function, thereby converting a normally regulated cell protein to one that is continuously active. It is believed that such deregulation of normal ras protein function is responsible for the transformation from normal to malignant growth.

The oligonucleotides of the present invention have also been used for modulating the expression of the raf gene, a naturally present cellular gene which occasionally converts to an activated form that has been implicated in abnormal cell proliferation and tumor formation.

The oligonucleotides of the present invention are also specifically hybridizable with nucleic acids relating to protein kinase C (PKC). These oligonucleotides have been found to modulate the expression of PKC.

The following examples and procedures illustrate the present invention and are not intended to limit the same.

EXAMPLE 1

Oligonucleotide Synthesis

Unsubstituted and substituted oligonucleotides were synthesized on an automated DNA synthesizer (Applied Biosystems model 380B) using standard phosphoramidite chemistry with oxidation by iodine. For phosphorothioate oligonucleotides, the standard oxidation bottle was replaced by 0.2 M solution of 3H-1,2-benzodithiole-3-one 1,1-dioxide in acetonitrile for the step wise thiation of the phosphite linkages. The thiation wait step was increased to 68 sec and was followed by the capping step. After cleavage from the CPG column and deblocking in concentrated ammonium hydroxide at 55° C. (18 hr), the oligonucleotides were purified by precipitating twice with 2.5 volumes of ethanol from a 0.5 M NaCl solution. Analytical gel electrophoresis was accomplished in 20% acrylamide, 8 M urea, 454 mM Tris-borate buffer, pH=7.0. Oligonucleoides and phosphorothioates were judged, based on polyacrylamide gel electrophoresis, to be greater than 80% full-length material.

EXAMPLE 2

Oligonucleotide Having 2'-Substituted Regions Flanking Central 2'-Deoxy Phosphorothioate Region A 15-mer RNA target of the sequence 5'GCGTTTTTTTTTTGCG 3' (SEQ ID NO:28) was prepared in the normal manner on the DNA sequencer using RNA protocols. A series of complementary phosphorothioate oligonucleotides having 2'-substituted nucleoside units in regions that flank a 2'-deoxy region were prepared utilizing 2'-substituted nucleoside precursors prepared as per known literature procedures, i.e. 2'-O-methyl, or as per the procedure of International Publication Number WO 92/03568, published Mar. 5, 1992. The 2'-substituted nucleosides were added as their 5'-O-dimethoxytrityl-3'-phosphoramidites in the normal manner on the DNA synthesizer. The complementary oligonucleotides have the sequence of 5' CGC AAA AAA AAA AAA ACG C 3' (SEQ ID NO:29). The 2'-substituent was located in CGC and CG regions of these oligonucleotides. The following 2'-O-substituents were used: 2'-fluoro; 2'-O-methyl; 2'-O-propyl; 2'-O-allyl; 2'-O-aminopropoxy; 2'-O-(methoxyethoxyethyl), 2'-O-imidazolebutoxy and 2'-0-imidazolepropoxy.

EXAMPLE 3

Ras-Luciferase Reporter Gene Assembly

The ras-luciferase reporter genes described in this study were assembled using PCR technology. Oligonucleotide primers were synthesized for use as primers for PCR cloning of the 5'-regions of exon 1 of both the mutant (codon-12) and non-mutant (wild-type) human H-ras genes. H-ras gene templates were purchased from the American Type Culture Collection (ATCC numbers 41000 and 41001) in Bethesda, Md. The oligonucleotide PCR primers ##5'-ACA-TTA-TGC-TAG-CTT-TTT-GAG-TAA-ACT-TGT-GGG-GCA-GGA-GAC-CCT-GT-3' (sense) (SEQ ID NO:15), and 5'-GAG-ATC-TGA-AGC-TTC-TGG-ATG-GTC-AGC-GC-3' (antisense) (SEQ ID NO:16), were used in standard PCR reactions using mutant and non-mutant H-ras genes as templates. These primers are expected to produce a DNA product of 145 base pairs corresponding to sequences −53 to +65 (relative to the translational initiation site) of normal and mutant H-ras, flanked by NheI and HindIII restriction endonuclease sites. The PCR product was gel purified, precipitated, washed and resuspended in water using standard procedures.

PCR primers for the cloning of the *P. pyralis* (firefly) luciferase gene were designed such that the PCR product would code for the full-length luciferase protein with the exception of the amino-terminal methionine residue, which would be replaced with two amino acids, an amino-terminal lysine residue followed by a leucine residue. The oligonucleotide PCR primers used for the cloning of the luciferase gene were 5'-GAG-ATC-TGA-AGC-TTG-AAG-ACG-CCA-AAA-ACA-TAA-AG-3' (sense) (SEQ ID NO:17), and 5'-ACG-CAT-CTG-GCG-CGC-CGA-TAC-CGT-CGA-CCT-CGA-3' (antisense) (SEQ ID NO:18), ##were used in standard PCR reactions using a commercially available plasmid (pT3/T7-Luc) (Clontech), containing the luciferase reporter gene, as a template. These primers were expected to yield a product of approximately 1.9 kb corresponding to the luciferase gene, flanked by HindIII and BssHII restriction endonuclease sites. This fragment was gel purified, precipitated, washed and resuspended in water using standard procedures.

To complete the assembly of the ras-luciferase fusion reporter gene, the ras and luciferase PCR products were digested with the appropriate restriction endonucleases and cloned by three-part ligation into an expression vector containing the steroid-inducible mouse mammary tumor virus promotor MMTV using the restriction endonucleases NheI, HindIII and BssHII. The resulting clone results in the insertion of H-ras 5' sequences (−53 to +65) fused in frame with the firefly luciferase gene. The resulting expression vector encodes a ras-luciferase fusion product which is expressed under control of the steroid-inducible MMTV promoter.

EXAMPLE 4
Transfection of Cells with Plasmid DNA

Transfections were performed as described by Greenberg (Current Protocols in Molecular Biology, Ausubel et al., eds.), John Wiley and Sons, NY), with the following modifications: HeLa cells were plated on 60 mm dishes at $5\times10^5$ cells/dish. A total of 10 µg of DNA was added to each dish, of which 9 µg was ras-luciferase reporter plasmid and 1 µg was a vector expressing the rat glucocorticoid receptor under control of the constitutive Rous sarcoma virus (RSV) promoter. Calcium phosphate-DNA coprecipitates were removed after 16–20 hours by washing with Tris-buffered saline [50 Mm Tris-Cl (pH 7.5), 150 mM NaCl] containing 3 mM EGTA. Fresh medium supplemented with 10% fetal bovine serum was then added to the cells. At this time, cells were pre-treated with antisense oligonucleotides prior to activation of reporter gene expression by dexamethasone.

EXAMPLE 5
Oligonucleotide Treatment of Cells

Immediately following plasmid transfection, cells were thrice washed with OptiMEM (GIBCO), and prewarmed to 37° C. 2 mL of OptiMEM containing 10 µg/mL N-[1-(2,3-dioleyloxy)propyl]-N,N,N,-trimethylammonium chloride (DOTMA) (Bethesda Research Labs, Gaithersburg, Md.) was added to each dish and oligonucleotides were added directly and incubated for 4 hours at 37° C. OptiMEM was then removed and replaced with the appropriate cell growth medium containing oligonucleotide. At this time, reporter gene expression was activated by treatment of cells with dexamethasone to a final concentration of 0.2 µM. Cells were harvested 12–16 hours following steroid treatment.

EXAMPLE 6
Luciferase Assays

Luciferase was extracted from cells by lysis with the detergent Triton X-100, as described by Greenberg (Current Protocols in Molecular Biology, Ausubel et al., eds., John Wiley and Sons, NY). A Dynatech ML1000 luminometer was used to measure peak luminescence upon addition of luciferin (Sigma) to 625 µM. For each extract, luciferase assays were performed multiple times, using differing amounts of extract to ensure that the data were gathered in the linear range of the assay.

EXAMPLE 7
Antisense Oligonucleotide Inhibition of ras-Luciferase Gene Expression A series of phosphorothioate oligonucleotides targeted to the codon-12 point mutation of activated H-ras were tested using the ras-luciferase reporter gene system described in the foregoing examples. This series comprised a basic sequence and analogs of that basic sequence. The basic sequence was of known activity as reported in International Publication Number WO 92/22651 identified above. In both, the basic sequence and its analogs, each of the nucleoside units incorporated phosphorothioate linkages to provide nuclease resistance. Each of the analogs incorporated nucleoside units that contained 2'-O-methyl substituents and 2'-deoxy-erythro-pentofuranosyl sugar moieties. In the analogs, a subsequence of the 2'-deoxy-erythro-pentofuranosyl sugar-containing subunits was flanked on both ends by subsequences of 2'-O-methyl substituted subunits. The analogs differed from one another with respect to the length of the subsequence of the 2'-deoxy-erythro-pentofuranosyl sugar containing nucleosides. The 2'-deoxy-erythro-pentofuranosyl nucleoside subsequences were centered at the point mutation of the codon-12 point mutation of the activated ras.

The oligonucleotide sequences, sequence reference numbers and sequence ID numbers (all are phosphorothioate analogs) are shown in Table 1. In this table those nucleosides identified with "$^M$" contain a 2'-O-methyl substituent and nucleosides identified with "$_d$" are 2'-deoxy-erythro-pentofur-anosyl nucleosides.

TABLE 1

Chimeric 2'-O-methyl P = S oligonucleotides

| OLIGO | SEQUENCE | SEQ ID NO: |
|---|---|---|
| 2570 | $C_dC_dA_dC_dA_dC_dC_dG_dA_dC_dG_dG_dC_dG_dC_dC_dC_d$ | 1 |
| 3975 | $C^MC^MA^MC^MA^MC^MC^MG^MA_dC^MG^MG^MC^MG^MC^MC^MC^M$ | 1 |
| 3979 | $C^MC^MA^MC^MA^MC^MC^MG_dA_dC_dG^MG^MC^MG^MC^MC^MC^M$ | 1 |
| 3980 | $C^MC^MA^MC^MA^MC^MC_dG_dA_dC_dG_dG^MC^MG^MC^MC^MC^M$ | 1 |
| 3985 | $C^MC^MA^MC^MA^MC_dC_dG_dA_dC_dG_dG_dC_dG^MC^MC^MC^M$ | 1 |
| 3984 | $C^MC^MA^MC^MA_dC_dC_dG_dA_dC_dG_dG_dC_dG^MC^MC^MC^M$ | 1 |

FIG. 1 shows dose-response data in which cells were treated with phosphorothioate oligonucleotides of Table 1. Oligonucleotide 2570 is targeted to the codon-12 point mutation of mutant (activated) H-ras RNA. The other nucleosides have 2'-O-methyl substituents thereon to increase binding affinity with sections of various lengths of interspaced 2'-deoxy-erythro-pentofuranosyl nucleosides. The control oligonucleotide is a random 20-mer phosphorothioate oligonucleotide. Results are expressed as percentage of luciferase activity in transfected cells not treated with oligonucleotide. As the figure shows, treatment of cells with increasing concentrations of oligonucleotide 2570 resulted in a dose-dependent inhibition of ras-luciferase activity in cells expressing the mutant form of ras-luciferase. Oligonucleotide 2570 displays an approximate threefold selectivity toward the mutant form of ras-luciferase as compared to the normal form.

As is further seen in FIG. 1, each of the oligonucleotides 3980, 3985 and 3984 exhibited greater inhibition of ras-luciferase activity than did oligonucleotide 2570. The greatest inhibition was displayed by oligonucleotide 3985 that has a 7-mer subsequence of 2'-deoxy-erythro-pentofuranosyl nucleosides. Oligonucleotide 3980, having a 5-mer subsequence of 2'-deoxy-erythro-pentofuranosyl nucleoside units exhibited the next greatest inhibition followed by oligonucleotide 3984 that has a 9-mer subsequence of 2'-deoxy-erythro-pentofuranosyl nucleoside units.

Figure 2:
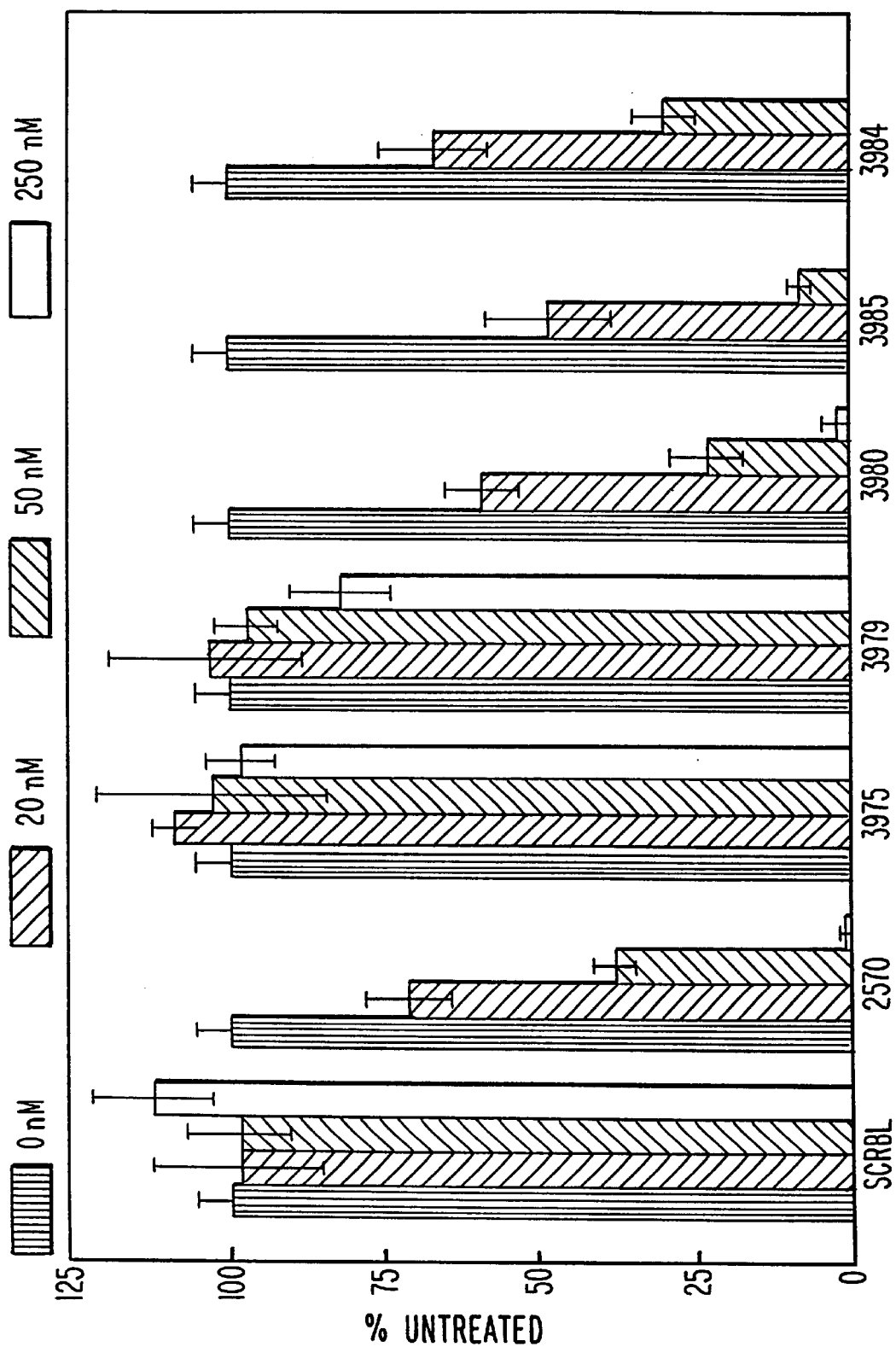
FIG. 2 is a bar graph showing dose response activity of oligonucleotides of the invention and reference compounds.

FIG. 2 shows results similar to FIG. 1, except that it is in the form of a bar graph. Further seen in FIG. 2 is the activity of oligonucleotide 3975 and oligonucleotide 3979. These oligonucleotides have subsequences of 2'-deoxy-erythro-pentofuranosyl nucleoside units 1 and 3 nucleosides in length, respectively. As is evident from FIG. 2, neither of the oligonucleotides showed significant activity. There was measurable activity observed for oligonucleotide 3979, having the 3-mer deoxy subsequence, at the highest concentration dose.

The increases in activity of oligonucleotides 3980, 3985 and 3984 compared to oligonucleotide 2570 is attributed to the increase in binding affinity imparted to these compounds by the 2'-O-methyl substituents located on the compounds and by the RNase H activation imparted to these compounds by incorporation of a subsequence of 2'-deoxy-erythro-pentofuranosyl nucleosides within the main sequence of nucleosides. In contrast to the active compounds of the invention, it is interesting to note that sequences identical to those of the active oligonucleotides 2570, 3980, 3985 and 3984 but having phosphodiester linkages instead of the phosphorothioate linkages of the active oligonucleotides of the invention showed no activity. This is attributed to phosphodiester compounds being substrates for nucleases that degrade phosphodiester compounds thus preventing them from potentially activating RNase H.

Other sugar modifications: The effects of other 2' sugar modifications besides 2'-O-methyl substituents on antisense activity in chimeric oligonucleotides have been examined. These modifications are listed in Table 2, along with the $T_m$ values obtained when 17-mer oligonucleotides having 2'-modified nucleosides flanking a 7-mer deoxy subsequence (or 7-mer deoxy gap) were hybridized with a 25-mer oligoribonucleotide complement as described in Example 8. A relationship was observed for these oligonucleotides between alkyl length at the 2' position and $T_m$. As alkyl length increased, $T_m$ decreased. The 2'-fluoro chimeric oligonucleotide displayed the highest $T_m$ of the series.

TABLE 2

Correlation of $T_m$ with Antisense Activity
2'-modified 17-mer with 7-deoxy gap
CCACACCGACGGCGCCC (SEQ ID NO:1)

| 2' MODIFICATION | $T_m$ (° C.) | IC$_{50}$ (nM) |
|---|---|---|
| Deoxy | 64.2 | 150 |
| O-Pentyl | 68.5 | 150 |
| O-Propyl | 70.4 | 70 |
| C-Methyl | 74.7 | 20 |
| Fluoro | 76.9 | 10 |

These 2' modified oligonucleotides were tested for antisense activity against H-ras using the transactivation reporter gene assay described in Example 9. All of these 2' modified chimeric compounds inhibited ras expression, with the 2'-fluoro 7-mer gapped compound being the most active. A 2'-fluoro chimeric oligonucleotide with a 5-mer central deoxy gap was also active.

Chimeric phosphorothioate oligonucleotides having SEQ ID NO:1 having 2'-O-propyl subsequences flanking a 5-mer or 7-mer deoxy subsequence were compared to 2'-O-methyl chimeric oligonucleotides. Expression of ras in T24 cells was inhibited by both 2'-O-methyl and 2'-O-propyl chimeric oligonucleotides with a 7-mer deoxy gap and a uniform phosphorothioate backbone. When the deoxy gap was decreased to five nucleosides, only the 2'-O-methyl oligonucleotide inhibited ras expression.

Antisense oligonucleotide inhibition of H-ras gene expression in cancer cells: Two phosphorothioate oligonucleotides (2502, 2503) complementary to the ras AUG region were tested as described in Example 10, along with chimeric oligonucleotides (4998, 5122) having the same sequence and 7-mer deoxy subsequences flanked by 2'-O-methyl subsequences. These chimeric oligonucleotides are shown in Table 3.

TABLE 3

Chimeric phosphorothioate oligonucleotides
having 2'-O-methyl ends (bold) and central
deoxy gap (AUG target)

| OLIGO | #DEOXY | SEQUENCE | SEQ ID NO: |
|---|---|---|---|
| 2502 | 20 | CTTATATTCCGTCATCGCTC | 2 |
| 4998 | 7 | CTTATATTCCGTCATCGCTC | 2 |
| 2503 | 20 | TCCGTCATCGCTCCTCAGGG | 3 |
| 5122 | 7 | TCCGTCATCGCTCCTCAGGG | 3 |

Compound 2503 inhibited ras expression in T24 cells by 71%, and the chimeric compound (4998) inhibited ras mRNA even further (84% inhibition). Compound 2502, also complementary to the AUG region, decreased ras RNA levels by 26% and the chimeric version of this oligonucleotide (5122) demonstrated 15% inhibition. Also included in this assay were two oligonucleotides targeted to the mutant codon-12. Compound 2570 (SEQ ID NO:1) decreased ras RNA by 82% and the 2'-O-methyl chimeric version of this oligonucleotide with a 7-mer deoxy subsequence (3985) decreased ras RNA by 95%.

Oligonucleotides 2570 and 2503 were also tested to determine their effects on ras expression in HeLa cells, which have a wild-type (i.e., not activated) H-ras codon-12. While both of these oligonucleotides inhibited ras expression in T24 cells (having activated codon-12), only the oligonucleotide (2503) specifically hybridizable with the ras AUG inhibited ras expression in HeLa cells. Oligonucleotide 2570 (SEQ ID NO:1), specifically hybridizable with the activated codon-12, did not inhibit ras expression in HeLa cells, because these cells lack the activated codon-12 target.

Oligonucleotide 2570, a 17-mer phosphorothioate oligonucleotide complementary to the codon-12 region of activated H-ras, was tested for inhibition of ras expression (as described in Example 8) in T24 cells along with chimeric phosphorothioate 2'-O-methyl substituted oligonucleotides 3980, 3985 and 3984, which have the same sequence as 2570 and have deoxy subsequences of 5, 7 and 9 nucleoside units, respectively (shown in Table 1). The uniform 2'-deoxy oligonucleotide 2570 and the three chimeric oligonucleotides decreased ras mRNA levels in T24 cells. Compounds 3985 (7-mer deoxy gap) and 3984 (9-mer deoxy gap) decreased ras mRNA by 81%; compound 3980 (5-mer deoxy gap) decreased ras mRNA by 81%. Chimeric oligonucleotides having this sequence, but having 2'-fluoro substituted nucleosides flanking a 5-mer deoxy (4689) or 7-mer deoxy (4690) subsequence, inhibited ras mRNA expression in T24 cells, with the 7-mer deoxy subsequence being preferred (82% inhibition, vs 63% inhibition for the 2'-fluoro chimera with a 5-mer deoxy subsequence)

Antisense oligonucleotide inhibition of proliferation of cancer cells: Three 17-mer oligonucleotides having the same sequence (SEQ ID NO:1), complementary to the codon-12 region of activated ras, were tested for effects on T24 cancer cell proliferation as described in Example 11. Oligonucleotide 3985 is a uniform phosphorothioate having a 7-mer deoxy subsequence flanked by 2'-O-methyl substituted nucleosides, and 4690 is a uniform phosphorothioate having a 7-mer deoxy subsequence (gap) flanked by 2'-fluoro substituted nucleosides ($C^F C^F A^F$ $C^F A^F C_d$ $C_d G_d A_d$ $C_d G_d G_d$ $C^F G^F C^F$ $C^F C^F$, SEQ ID NO:1, nucleosides identified with "F" contain a 2'-fluoro substituent and nucleosides identified with "d" are 2'-deoxy-erythro-pentofuranosyl nucleosides). Effects of these oligonucleotides on cancer cell proliferation correlated well with their effects on ras mRNA expression shown by Northern blot analysis: oligonucleotide 2570 inhibited cell proliferation by 61%, the 2'-O-methyl chimeric oligonucleotide 3985 inhibited cell proliferation by 82%, and the 2'-fluoro chimeric analog inhibited cell proliferation by 93%.

In dose-response studies of these oligonucleotides on cell proliferation, the inhibition was shown to be dose-dependent in the 25 nM to 100 nM range. ICso values of 44 nM, 61 nM and 98 nM could be assigned to oligonucleotides 4690, 3985 and 2570, respectively. The random oligonucleotide control had no effect at the doses tested.

The effect of ISIS 2570 on cell proliferation was cell type-specific. The inhibition of T24 cell proliferation by this oligonucleotide was four times as severe as the inhibition of HeLa cells by the same oligonucleotide (100 nM oligonucleotide concentration). ISIS 2570 is targeted to the activated (mutant) ras codon-12, which is present in T24 but lacking in HeLa cells, which have the wild-type codon-12.

Chimeric backbone-modified oligonucleotides: Oligonucleotides discussed in previous examples have had uniform phosphorothioate backbones. The 2' modified chimeric oligonucleotides discussed above are not active in uniform phosphodiester backbones. A chimeric oligonucleotide was synthesized (ISIS 4226) having 2'-O-methyl substituted regions flanking a 5-mer deoxy gap, with the gap region having P=S linkages and the flanking regions having P=O linkages. Another chimeric oligonucleotide (ISIS 4223) having a P=O backbone in the gap and P=S in flanking regions was also made. These oligonucleotides are shown in Table 4.

Oligonucleotides having uniform 2'-deoxy nucleoside units were also synthesized. These oligonucleotides have phosphorothioate linkages with either a single phosphodiester (ISIS 4248), two phosphodiester (ISIS 4546), three phosphodiester (ISIS 4551), four phosphodiester (ISIS 4593), five phosphodiester (ISIS 4606) or ten phosphodiester linkages (ISIS-4241) in the central region of the molecule. These oligonucleotides are also shown in Table 4.

TABLE 4

Chimeric backbone (P = S/P = O) oligonucleotides having 2'-O-methyl wings (bold) and central deoxy gap (backbone linkages indicated by s (P = S) or o (P = O)

| OLIGO # | P=S | SEQUENCE | SEQ ID NO: |
|---|---|---|---|
| 2570 | 16 | CsCsAsCsAsCsCsGsAsCsGsGsCsGsCsC | 1 |
| 4226 | 5 | CoCoAoCoAoCsCsGsAsCsGoGoCoGoCoCoC | 1 |
| 4233 | 11 | CsCsAsCsAsCoCoGoAoCoGsGsCsGsCsC | 1 |
| 4248 | 15 | CsCsAsCsAsCsCsGsAoCsGsGsCsGsCsC | 1 |
| 4546 | 14 | CsCsAsCsAsCsCsGsAoCoGsGsCsGsCsC | 1 |
| 4551 | 13 | CsCsAsCsAsCsCsGoAoCoGsGsCsGsCsC | 1 |
| 4593 | 12 | CsCsAsCsAsCsCoGoAoCoGsGsCsGsCsC | 1 |
| 4606 | 11 | CsCsAsCsAsCoCoGoAoCoGsGsCsGsCsC | 1 |
| 4241 | 6 | CsCsAsCoAoCoCoGoAoCoGoGoCoGsCsC | 1 |

Oligonucleotides were incubated in crude HeLa cellular extracts at 37° C. to determine their sensitivity to nuclease degradation as described in Dignam et al., *Nucleic Acids Res.*, 1983, 11, 1475–1489. The oligonucleotide (4233) with a 5-mer phosphodiester central region and phosphorothioate/2'-O-methyl substituted flanking regions had a $T_{1/2}$ of 7 hr. The oligonucleotide with a 5-mer phosphorothioate central region and phosphorothioate/2'-O-methyl substituted flanking regions had a $T_{1/2}$ of 30 hours. In the set of oligonucleotides having 1 to 10 phosphodiester diester linkages, the oligonucleotide (4248) with a single phosphodiester linkage was as stable to nucleases as was the uniform phosphorothioate oligonucleotide, ISIS 2570, showing no degradation after 5 hours in HeLa cell extract. Oligonucleotides with 2-mer, 3-mer and 4-mer phosphodiester central regions had $T_{1/2}$s of approximately 5.5 hours, 3.75 hours, and 3.2 hours, respectively, and oligonucleotides with 5-mer or 10-mer phosphodiester central regions had $T_{1/2}$s of 1.75 hours and 0.9 hours, respectively.

Antisense activity of chimeric backbone-modified oligonucleotides: A uniform phosphorothioate backbone is not required for antisense activity. ISIS 4226 and ISIS 4233 were tested in the ras-luciferase reporter system for effect on ras expression along with ISIS 2570 (uniform phosphorothioate/uniform deoxy), ISIS 3980 (uniform phosphorothioate, 2'-O-methyl flanking regions with deoxy central region) and ISIS 3961 (uniform phosphodiester, 2'-O-methyl flanking regions with deoxy central region). All of the oligonucleotides having a P=S (i.e., nuclease-resistant) central region inhibited ras expression. The two uniform 2'-deoxy oligonucleotides having phosphorothioate linkages containing either 1 phosphodiester (ISIS 4248) or 10 phosphodiester linkages (ISIS 4241) in the center of the molecule were also assayed for activity. The oligonucleotide containing a single P=O was just as active as the oligonucleotide containing all phosphorothioate linkages (uniform P=S oligonucleotide), while the same oligonucleotide containing 10 P=O linkages was completely inactive.

Chimeric phosphorothioate oligonucleotides of SEQ ID NO: 1 were made, having a phosphorothioate backbone in the 7-mer deoxy central region (gap) and phosphodiester linkages in the flanking regions, which were either 2'-O-methyl or 2'-O-propyl substituted. The oligonucleotide with 2'-O-propyl substituted phosphodiester flanking regions was able to inhibit ras expression.

EXAMPLE 8

Melting Curves

Absorbance vs. temperature curves were measured at 260 nm using a Gilford 260 spectrophotometer interfaced to an IBM PC computer and a Gilford Response II spectrophotometer. The buffer contained 100 mM $Na^+$, 10 mM phosphate and 0.1 mM EDTA, pH 7. Oligonucleotide concentration was 4 $\mu$M each strand determined from the absorbance at 85° C. and extinction coefficients calculated according to Puglisi and Tinoco, *Methods in Enzymol.*, 1989, 180, 304–325. $T_m$ values, free energies of duplex formation and association constants were obtained from fits of data to a two state model with linear sloping baselines. Petersheim, M. and Turner, D. H., *Biochemistry*, 1983, 22, 256–263. Reported parameters are averages of at least three experiments. For some oligonucleotides, free energies of duplex formation were also obtained from plots of $T_m^{-1}$ vs $1\log_{10}$ (concentration). Borer, P. N., Dengler, B., Tinoco, I., Jr., and Uhlenbeck, O. C., *J. Mol. Biol.*, 1974, 86, 843–853.

EXAMPLE 9 ras Transactivation Reporter Gene System

The expression plasmid pSV2-oli, containing an activated (codon-12, GGC→GTC) H-ras cDNA insert under control of the constitutive SV40 promoter, was a gift from Dr. Bruno Tocque (Rhone-Poulenc Sante, Vitry, France). This plasmid was used as a template to construct, by PCR, a H-ras expression plasmid under regulation of the steroid-inducible mouse mammary 30 tumor virus (MMTV) promoter. To obtain H-ras coding sequences, the 570 bp coding region of the H-ras gene was amplified by PCR. The PCR primers were designed with unique restriction endonuclease sites in their 5'-regions to facilitate cloning. The PCR product containing the coding region of the H-ras 35 codon-12 mutant oncogene was gel purified, digested, and gel purified once again prior to cloning. This construction was completed by cloning the insert into the expression plasmid pMAMneo (Clontech Laboratories, Calif..

The ras-responsive reporter gene pRDO53 was used to detect ras expression. Owen et al., *Proc. Natl. Acad. Sci. U.S.A.*, 1990, 87, 3866–3870.

EXAMPLE 10
Northern Blot Analysis of ras Expression in vivo

The human urinary bladder cancer cell line T24 was obtained from the American Type Culture Collection (Rockville Md.). Cells were grown in McCoy's 5A medium with L-glutamine (Gibco BRL, Gaithersburg Md.), supplemented with 10% heat-inactivated fetal calf serum and 50 U/mL each of penicillin and streptomycin. Cells were seeded on 100 mm plates. When they reached 70% confluency, they were treated with oligonucleotide. Plates were washed with 10 mL prewarmed PBS and 5 mL of OptiMEM reduced-serum medium containing 2.5 µL DOTMA. Oligonucleotide was then added to the desired concentration. After 4 hours of treatment, the medium was replaced with McCoy's medium. Cells were harvested 48 hours after oligonucleotide treatment and RNA was isolated using a standard CsCl purification method. Kingston, R. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, NY.

The human epithelioid carcinoma cell line HeLa 229 was obtained from the American Type Culture Collection (Bethesda, Md.). HeLa cells were maintained as monolayers on 6-well plates in Dulbecco's Modified Eagle's medium (DMEM) supplemented with 10% fetal bovine serum and 100 U/mL penicillin. Treatment with oligonucleotide and isolation of RNA were essentially as described above for T24 cells.

Northern hybridization: 10 µg of each RNA was electrophoresed on a 1.2% agarose/formaldehyde gel and transferred overnight to GeneBind 45 nylon membrane (Pharmacia LKB, Piscataway, N.J.) using standard methods. Kingston, R. E. in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, NY. RNA was UV-crosslinked to the membrane. Double-stranded $^{32}$P-labeled probes were synthesized using the Prime a Gene labeling kit (Promega, Madison Wis.). The ras probe was a SalI-NheI fragment of a cDNA clone of the activated (mutant) H-ras mRNA having a GGC-to-GTC mutation at codon-12. The control probe was G3PDH. Blots were prehybridized for 15 minutes at 68° C. with the QuickHyb hybridization solution (Stratagene, La Jolla, Calif.). The heat-denatured radioactive probe (2.5×10$^6$ counts/2 mL hybridization solution) mixed with 100 µL of 10 mg/mL salmon sperm DNA was added and the membrane was hybridized for 1 hour at 68° C. The blots were washed twice for 15 minutes at room temperature in 2×SSC/0.1% SDS and once for 30 minutes at 60° C. with 0.1×SSC/0.1%SDS. Blots were autoradiographed and the intensity of signal was quantitated using an ImageQuant PhosphorImager (Molecular Dynamics, Sunnyvale, Calif.). Northern blots were first hybridized with the ras probe, then stripped by boiling for 15 minutes in 0.1×SSC/0.0%SDS and rehybridized with the control G3PDH probe to check for correct sample loading.

EXAMPLE 11
Antisense Oligonucleotide Inhibition of Proliferation of Cancer Cells Cells were cultured and treated with oligonucleotide essentially as described in Example 10. Cells were seeded on 60 mm plates and were treated with oligonucleotide in the presence of DOTMA when they reached 70% confluency. Time course experiment: On day 1, cells were treated with a single dose of oligonucleotide at a final concentration of 100 nM. The growth medium was changed once on day 3 and cells were counted every day for 5 days, using a counting chamber. Dose-response experiment: Various concentrations of oligonucleotide (10, 25, 50, 100 or 250 nM) were added to the cells and cells were harvested and counted 3 days later. Oligonucleotides 2570, 3985 and 4690 were tested for effects on T24 cancer cell proliferation.

EXAMPLE 12
Inhibition of PKC-α mRNA Expression by Chimeric (Deoxy Gapped) 2'-O-methyl Oligonucleotides Oligonucleotides having SEQ ID NO:4 were synthesized as uniform phosphorothioate chimeric oligonucleotides having a deoxy central region or deoxy gap of varying lengths flanked by 2'-O-methyl substituted subsequences. These oligonucleotides (500 nM concentration) were tested for effects on PKC-α mRNA levels by Northern blot analysis. Deoxy gaps of 8 nucleosides or more gave maximal reduction of PKC-α mRNA levels (both transcripts) in all cases. These oligonucleotides reduced PKC-α mRNA by approximately 83% with a deoxy gap length of 4 nucleosides, and gave nearly complete reduction of PKC-α MRNA with a deoxy gap length of 6 or more nucleosides.

The 2'-O-methyl substituted chimeric oligonucleotides with 4-mer or 6-mer deoxy gaps have an IC$_{50}$ for PKC-α mRNA reduction (concentration of oligonucleotide needed to give a 50% reduction in KKC-α mRNA levels) of 200 nM to 250 nM, as did the uniform deoxy oligonucleotide (all are uniform phosphorothioates). The 2'-O-methyl substituted chimeric oligonucleotide with an 8-mer deoxy gap had an IC$_{50}$ of approximately 85 nM.

Several variations of this chimeric oligonucleotide (SEQ. ID NO: 4) were compared for ability to lower PKC-α mRNA levels. These oligonucleotides are shown in Table 5.

TABLE 5

Chimeric 2'-O-methyl deoxy P = S oligonucleotides
bold = 2'-O-methyl; s = P = S linkage, o = P = O linkage

| OLIGO | SEQUENCE | SEQ ID NO: |
|---|---|---|
| 3522 | AsAsAsAsCsGsTsCsAsGsCsCsAsTsGsGsTsCsCsC | 4 |
| 5352 | AsAsAsAsCsGsTsCsAsGsCsCsAsTsGsGsTsCsCsC | 4 |
| 6996 | AoAoAoAoCoGsTsCsAsGsCsCsAsTsGoGoToCoCoC | 4 |
| 7008 | AsAoAoAoCoGsTsCsAsGsCsCsAsTsGoGoToCoCsC | 4 |
| 7024 | AsAoAoAoCoGsToCsAoGsCoCsAsTsGoGoToCoCsC | 4 |

Figure 3:
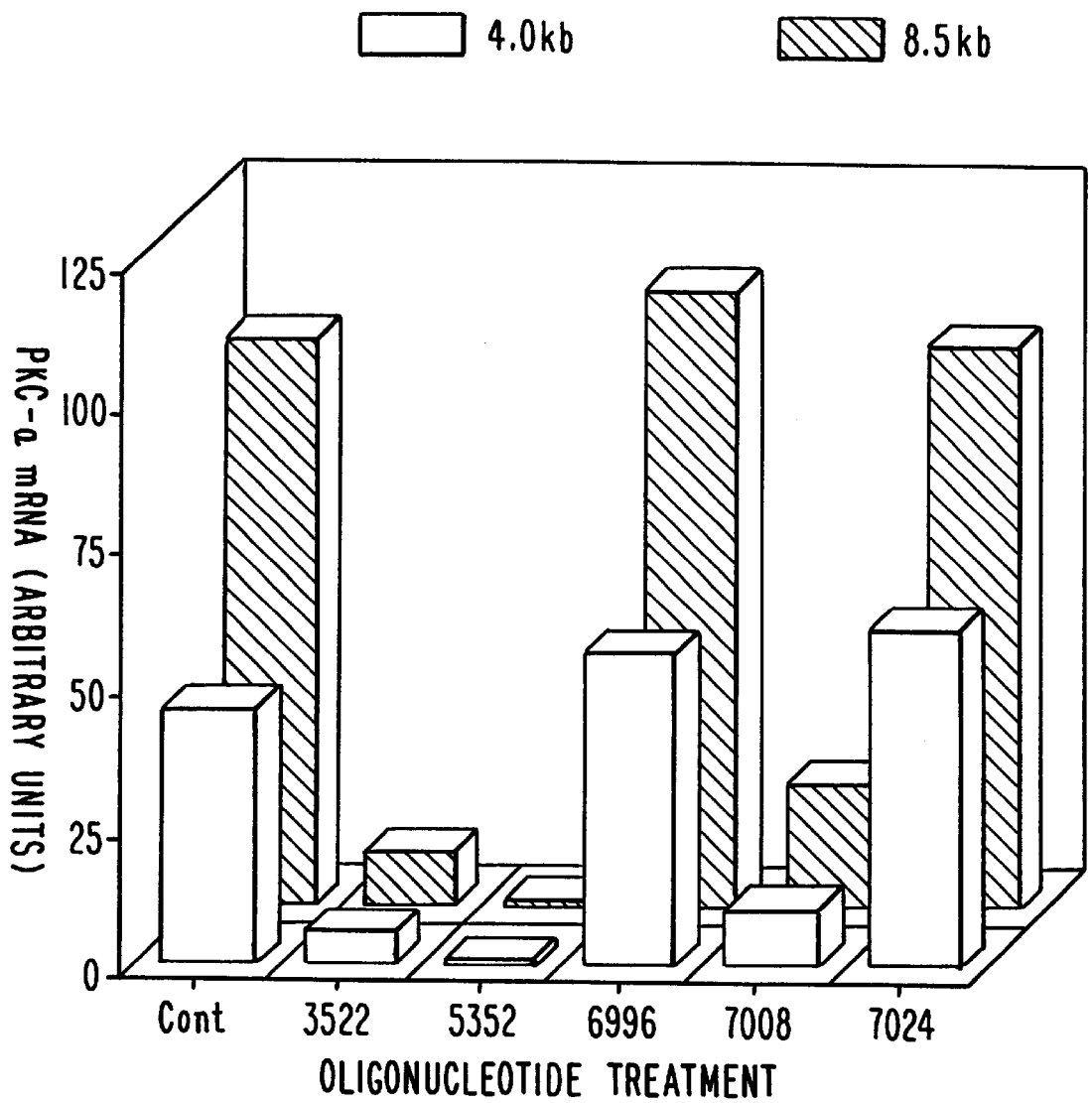
FIG. 3 is a bar graph showing the effects of several 2'-O-methyl chimeric oligonucleotides on KKC-α mRNA levels. Hatched bars represent the 8.5 kb transcript, and plain bars represent the 4.0 kb transcript.

Effect of these oligonucleotide's on PKC-α mRNA levels is shown in FIG. 3. Oligonucleotides 7008, 3522 and 5352 show reduction of PKC-α mRNA, with 5352 being most active.

A series of 2'-O-propyl chimeric oligonucleotides was synthesized having SEQ ID NO:4. These oligonucleotides are shown in Table 6.

TABLE 6

Chimeric 2'-O-propyl deoxy P = S oligonucleotides
bold = 2'-O-propyl; s = P = S linkage, o = P = O linkage

| OLIGO | SEQUENCE | SEQ ID NO: |
|---|---|---|
| 7199 | AsAsAsAsCsGsTsCsAsGsCsCsCsAsTsGsGsTsCsC | 4 |
| 7273 | AoAoAoAoCoGsTsCsAsGsCsCsCsAsTsGoGoToCoCoC | 4 |
| 7294 | AsAoAoAoCoGsTsCsAsGsCsCsCsAsTsGoGoToCoCsC | 4 |
| 7295 | AsAoAoAoCoGsToCsAoGsCoCsAsTsGoGoToCoCsC | 4 |

Figure 4:
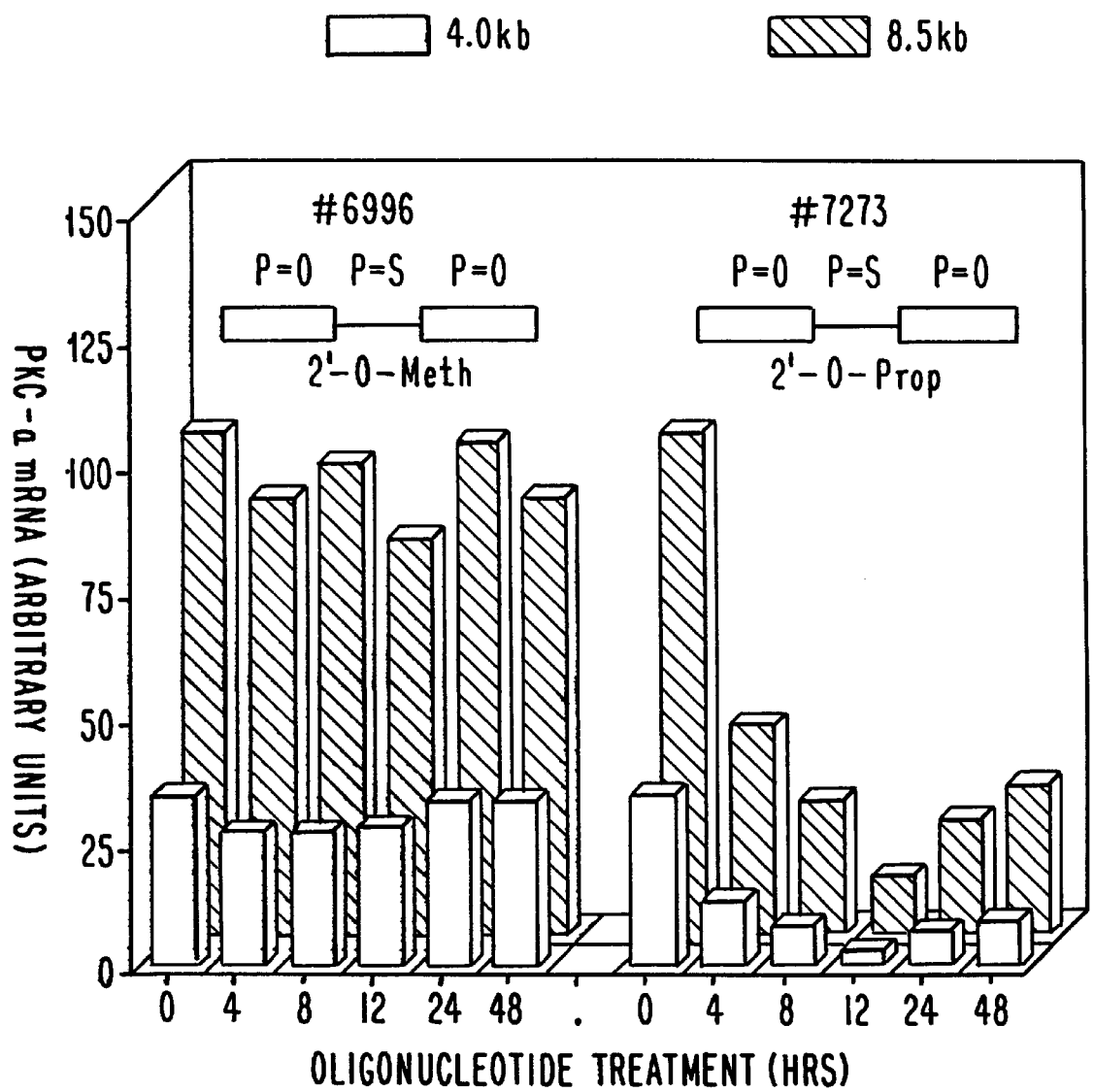
FIG. 4 is a bar graph showing the effects of several 2'-O-methyl and 2'-O-propyl chimeric oligonucleotides on KKC-α mRNA levels. Hatched bars represent the 8.5 kb transcript, and plain bars represent the 4.0 kb transcript.
Figure 5:
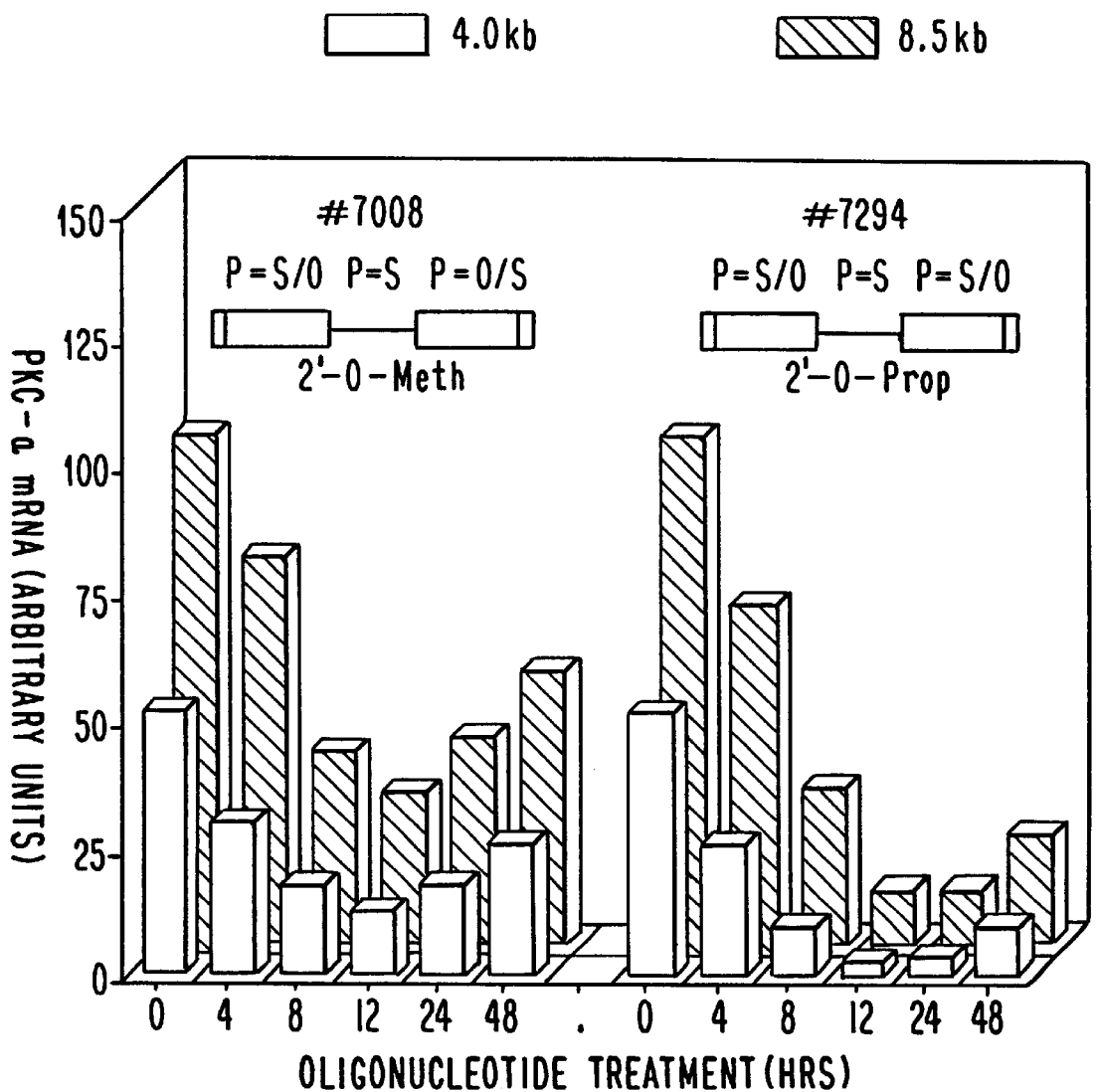
FIG. 5 is a bar graph showing the effects of additional 2'-O-methyl and 2'-O-propyl chimeric oligonucleotides on KKC-α mRNA levels. Hatched bars represent the 8.5 kb transcript, and plain bars represent the 4.0 kb transcript.

These 2'-O-propyl substituted chimeric oligonucleotides were compared to the 2'-O-methyl substituted chimeric oligonucleotides. Oligonucleotides 7273 and 7294 were more active than their 2'-O-methyl counterparts at lowering PKC-α mRNA levels. This is shown in FIGS. 4 and 5.

EXAMPLE 13
Additional Oligonucleotides which Decrease PKC-α MRNA Expression

Additional phosphorothioate oligonucleotides targeted to the human PKC-α 3'-untranslated region were designed and synthesized. These sequences are shown in Table 7.

TABLE 7

Chimeric 2'-O-propyl deoxy P = S oligonucleotides targeted to PKC-α3'-UTR
bold = 2'-O-propyl; s = P = S linkage, o =P = O linkage

| OLIGO | SEQUENCE | | | | | | SEQ ID NO: |
|---|---|---|---|---|---|---|---|
| 6632 | TsTsCs | TsCsGs | CsTsGs | GsTsGs | AsGsTs | TsTsC | 5 |
| 6653 | TsTsCs | TsCsGs | CsTsGs | GsTsGs | AsGsTs | TsTsC | 5 |
| 6665 | ToToCo | TsCsGs | CsTsGs | GsTsGs | AsGsTo | ToToC | 5 |
| 7082 | TsCsTs | CsGsCs | TsGsGs | TsGsAs | GsTsTs | TsC | 6 |
| 7083 | TsCsTs | CsGsCs | TsGsGs | TsGsAs | GsTsTs | TsC | 6 |
| 7084 | ToCoTo | CsGsCs | TsGsGs | TsGsAs | GsToTo | ToC | 6 |

Oligonucleotides 6632, 6653, 7082 and 7083 are most active in reducing PKC-α mRNA levels.

EXAMPLE 14
Effect-of Oligonucleotides Having SEQ ID NO: 30 on PKC-α mRNA Levels

A549 cells were treated with phosphorothioate oligonucleotides at 500 nM for 4 hours in the presence of the cationic lipids DOTMA/DOPE, washed and allowed to recover for an additional 20 hours. Total RNA was extracted and 20 μg of each was resolved on 1.2% gels and transferred to nylon membranes. These blots were probed with a $^{32}$p radiolabeled PKC-α cDNA probe and then stripped and reprobed with a radiolabeled G3PDH probe to confirm equal RNA loading. Each oligonucleotide [3520 (SEQ ID NO:3), 3521 (SEQ ID NO: 30), 3522 (SEQ ID NO: 4) and. 3527 SEQ ID NO: 32)] was used in duplicate. The two major PKC-α transcripts (8.5 kb and 4.0 kb) were examined and quantified with a PhosphorImager (Molecular Dynamics, Sunnyvale Calif.). ISIS 3521 (SEQ ID NO: 30) gave approximately 80% reduction of the smaller transcript and over 90% reduction of the larger transcript.

Two oligonucleotides having SEQ ID NO: 30 and an 8-mer deoxy central region flanked on each side by nucleosides having a 2'-OCH$_2$CH$_2$OCH$_3$ modification were synthesized. For ease of synthesis, the last nucleoside was a deoxynucleoside. These compounds, shown in Table 8, differ in that one of them, ISIS 9606, has a uniform phosphorothioate backbone while the other, ISIS 9605, has a phosphorothioate backbone in the central region (backbone linkages 7–14) and a phosphodiester backbone in the flanking regions. These oligonucleotides were tested for their ability to inhibit PKC-α mRNA expression in A549 cells, in comparison to the phosphorothioate compound, ISIS 3521. The results are shown in FIGS. 6a and 6b. IC$_{50}$s were calculated (oligonucleotide concentration yielding 50% inhibition) for the three compounds. The phosphorothioate compound, ISIS 3521, showed an IC$_{50}$ of approximately 170 nM. Both the methoxyethoxy compounds, ISIS 9605 and 9606, showed IC$_{50}$s of approximately 25 nM. This 6- to 7-fold increase in potency with the methoxyethoxy modification was an indication of surprising activity. Because of their extremely low IC$_{50}$s, the methoxyethoxy compounds 9605 and 9606 are preferred.

TABLE 8

Oligonucleotides having SEQ ID NO: 30

Figure 7A:
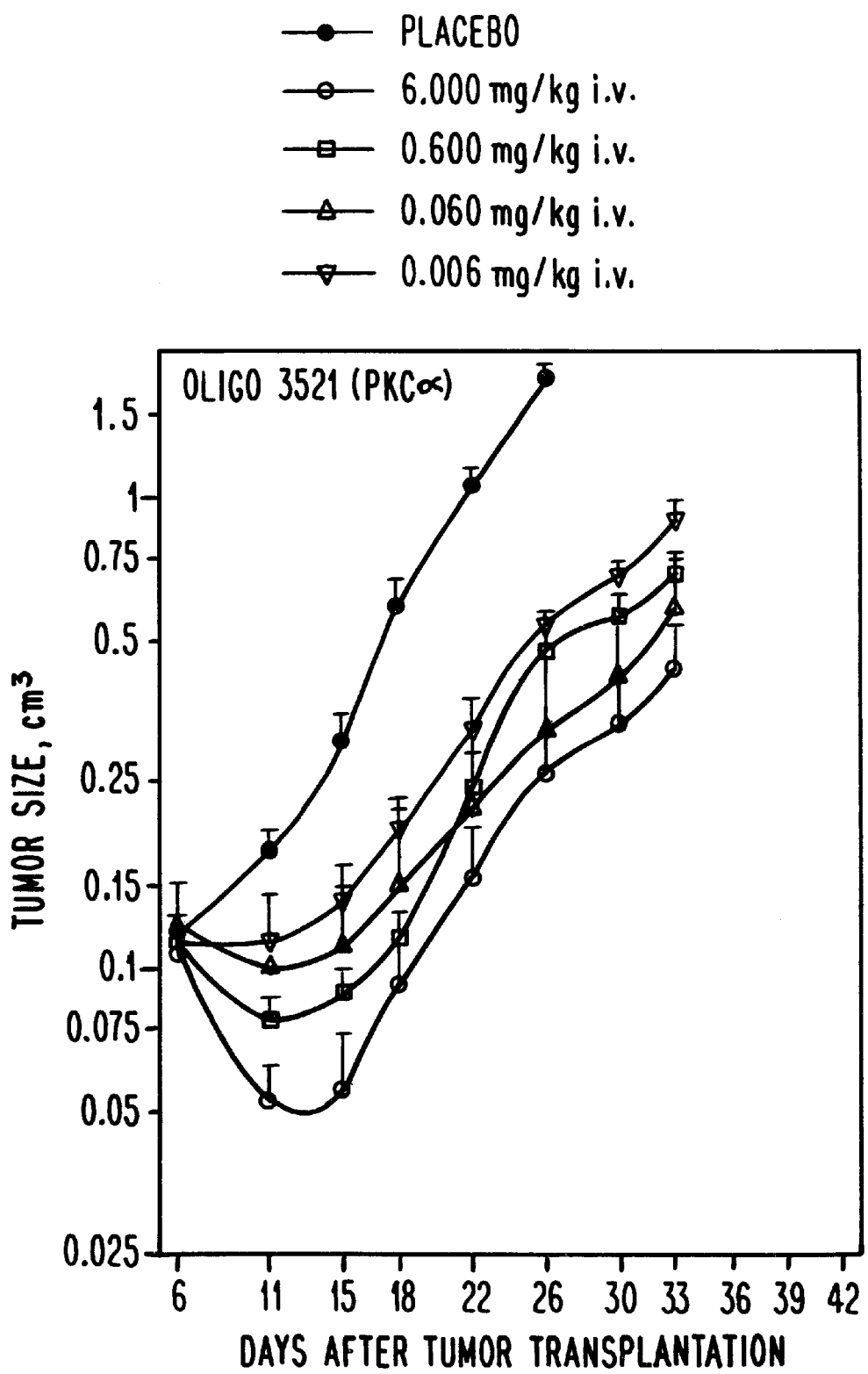
FIGS. 7a and 7b are line graphs showing the effects of oligonucleotides having SEQ ID NO: 30 on the growth of human colon carcinoma (Colo 205) tumor xenografts in nude mice.
Figure 7B:
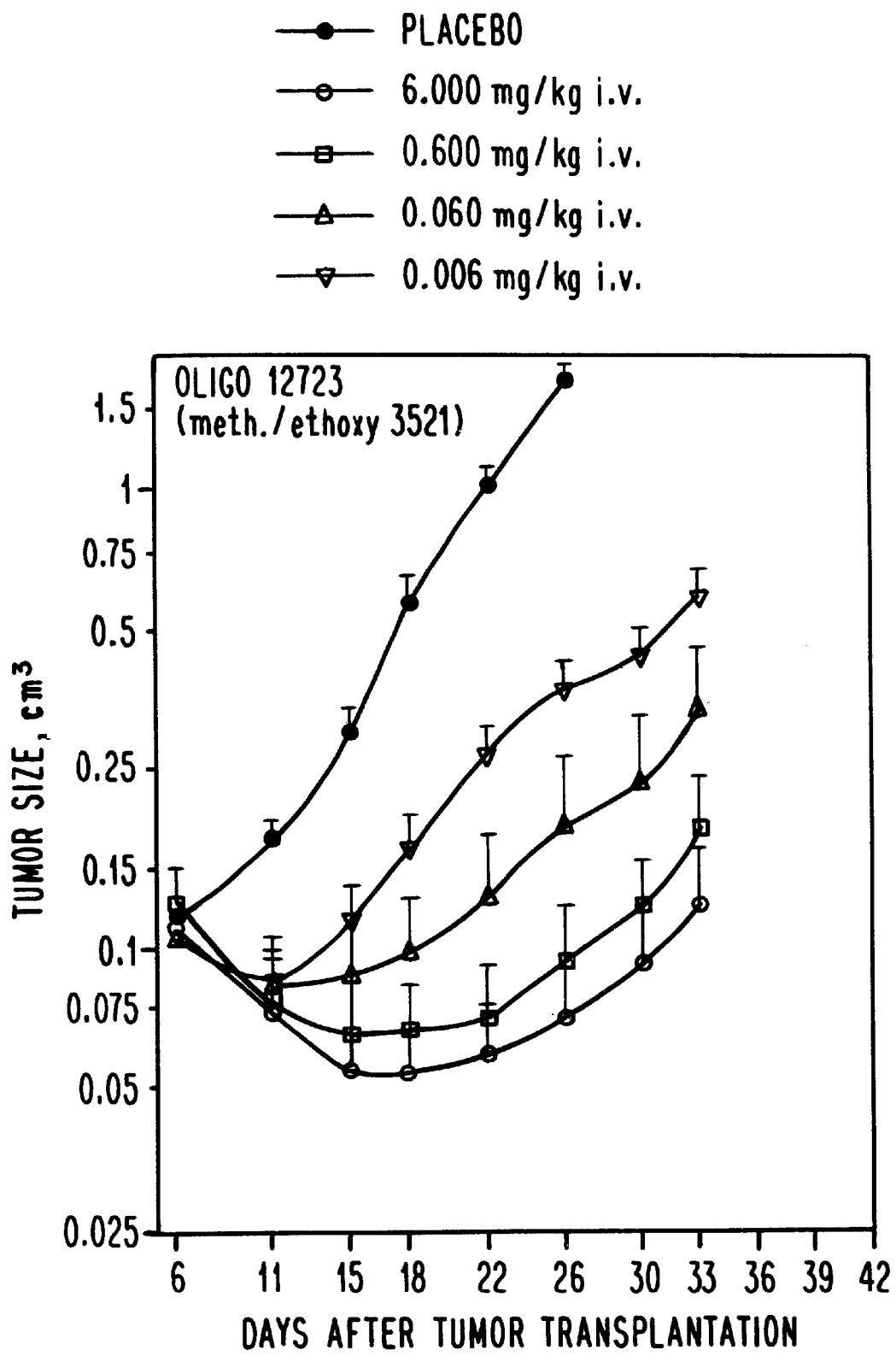

| ISIS # | SEQUENCE |
|---|---|
| 3521 | GsTsTsCsTsCsGsCsTsGsGsTsGsAsGsTsTsTsCsA |
| 9605 | GoToToCoToCsGsCsTsGsGsTsGsAsGoToToToCoA |
| 9606 | GsTsTsCsTsCsGsCsTsGsGsTsGsAsGsTsTsTsCsA |
| 12723 | GoToToCoToCsGsCsTsGsGsTsGsAsGoToToToCoA | bold= 2'-OCH$_2$CH$_2$OCH$_3$
s= phosphorothioate (P = S) linkage
o= phosphodiester (P = O) linkage EXAMPLE 15
Effect of the 2'-Methoxyethoxy Oligonucleotide ISIS 12723 on the Growth of Human Colo-205 Colon Tumors in Nude Mice Subcutaneous human Colo-205 colon carcinoma xenografts in nude mice were established by injection of 5×10$^6$ Colo-205 cells under the skin. Mice were treated with ISIS 12723 (SEQ ID NO: 30), an oligonucleotide having an 8-mer deoxy central region flanked on each side by 6-mer subsequences having a 2'-OCH$_2$CH$_2$OCH$_3$ modification, a phosphorothioate backbone in the central region (backbone linkages 7–14) and a phosphodiester backbone in the flanking regions, or ISIS 3521 (SEQ ID NO: 30, uniform deoxy phosphorothioate, administered intravenously once per day at a dosage of 0.006, 0.06, 0.6 or 6.0 mg/kg. In this study, ISIS 12723 inhibited tumor growth by over 95% compared to saline placebo controls (FIG. 7b), and ISIS 3521 inhibited tumor growth by over 83% compared to controls (FIG. 7a). The methoxyethoxy compound, ISIS 12723, is therefore preferred.

EXAMPLE 16
Inhibition of c-raf Expression by Chimeric Oligonucleotides

Chimeric oligonucleotides having SEQ ID NO:7 were designed using the Genbank c-raf sequence HUMRAFR (Genbank listing x03484), synthesized and tested for inhibition of c-raf mRNA expression in T24 bladder carcinoma cells using a Northern blot assay. These chimeric oligonucleotides have central "gap" regions of 6, 8 or 10 deoxy nucleosides flanked by two regions of 2'-O-methyl modified nucleosides, and are shown in Table 9. Backbones were uniformly phosphorothioate. In a Northern blot analysis, as described in Example 20, all three of these oligonucleotides (ISIS 6720, 6-mer deoxy gap; ISIS 6717, 8-mer deoxy gap;

ISIS 6729, 10-mer deoxy gap) showed greater than 70% inhibition of c-raf mRNA expression in T24 cells. These oligonucleotides are preferred. The oligonucleotide with an 8-mer deoxy gap (6717) showed greater than 90% inhibition and is more preferred.

TABLE 9

Chimeric 2'-O-methyl P = S deoxy "gap"oligo-
nucleotides bold= 2'-O-methyl

| OLIGO | SEQUENCE | Target site | SEQ ID NO: |
|---|---|---|---|
| 6720 | TCCCGCCTGTGACATGCATT | 3'UTR | 7 |
| 6717 | TCCCGCCTGTGACATGCATT | 3'UTR | 7 |
| 6729 | TCCCGCCTGTGACATGCATT | 3'UTR | 7 |

Additional chimeric oligonucleotides were synthesized having one or more regions of 2'-O-methyl modification and uniform phosphorothioate backbones. These are shown in Table 10. All are phosphorothioates; bold regions indicate 2'-O-methyl modified regions.

TABLE 10

Chimeric 2'-O-methyl P = S c-raf oligonucleotides

| OLIGO | SEQUENCE | Target site | SEQ ID NO: |
|---|---|---|---|
| 7848 | TCCTCCTCCCCGCGGCGGGT | 5'UTR | 8 |
| 7852 | TCCTCCTCCCCGCGGCGGGT | 5'UTR | 8 |
| 7849 | CTCGCCCGCTCCTCCTCCCC | 5'UTR | 9 |
| 7851 | CTCGCCCGCTCCTCCTCCCC | 5'UTR | 9 |
| 7856 | TTCTCGCCCGCTCCTCCTCC | 5'UTR | 10 |
| 7855 | TTCTCGCCCGCTCCTCCTCC | 5'UTR | 10 |
| 7854 | TTCTCCTCCTCCCCTGGCAG | 3'UTR | 11 |
| 7847 | CTGGCTTCTCCTCCTCCCCT | 3'UTR | 12 |
| 7850 | CTGGCTTCTCCTCCTCCCCT | 3'UTR | 12 |
| 7853 | CCTGCTGGCTTCTCCTCCTC | 3'UTR | 13 |
| 9355 | CGGGAGGCGGTCACATTCGG | 5'UTR | 19 |

When tested for their ability to inhibit c-raf mRNA by Northern blot analysis, ISIS 7848, 7849, 7851, 7856, 7855, 7854, 7847, and 7853 gave better than 70% inhibition and are therefore preferred. of these, 7851, 7855, 7847 and 7853 gave greater than 90% inhibition and are more preferred.

Additional chimeric oligonucleotides with various 2' modifications were prepared and tested. These are shown in Table 11. All are phosphorothioates; bold regions indicate 2'-modified regions.

TABLE 11

Chimeric 2'-modified P = S c-raf oligonucleotides

| OLIGO | SEQUENCE | TARGET SITE | MODIFIC. | SEQ ID NO: |
|---|---|---|---|---|
| 6720 | TCCCGCCTGTGACATGCATT | 3'UTR | 2'-C-Me | 7 |
| 6717 | TCCCGCCTGTGACATGCATT | 3'UTR | 2'-O-Me | 7 |
| 6729 | TCCCGCCTGTGACATGCATT | 3'UTR | 2'-O-Me | 7 |
| 8097 | TCTGGCGCTGCACCACTCTC | 3'UTR | 2'-O-Me | 14 |
| 9270 | TCCCGCCTGTGACATGCATT | 3'UTR | 2'-O-Pr | 7 |
| 9058 | TCCCGCCTGTGACATGCATT | 3'UTR | 2'-F | 7 |
| 9057 | TCTGGCGCTGCACCACTCTC | 3'UTR | 2'-F | 14 |

Of these, oligonucleotides 6720, 6717, 6729, 9720 and 9058 are preferred. Oligonucleotides 6717, 6729, 9720 and 9058 are more preferred.

EXAMPLE 17
Effect of 2'-Methoxyethoxy Oligonucleotides Having SEQ ID NO: 7 on c-raf mRNA Expression Two oligonucleotides having SEQ ID NO: 7 and a central 8-nucleoside unit subsequence containing 2'-deoxy-erythro-pentofuranosyl sugar moieties flanked on each side by 6 nucleoside unit subsequences having 2'-O—$CH_2$—$CH_2$—O—$CH_3$ modifications were synthesized. These compounds differ in that one of them, ISIS 10755 (also known as CIBA 1440) has a uniform phosphorothioate backbone; the other, ISIS 10754 (also known as CIBA 1439 or CGP 69845) has phosphorothioate linkages in the central region (linkages 7–14) and phosphodiester linkages in the flanking regions. These oligonucleotides were tested for their ability to inhibit c-raf mRNA expression in T24 cells. $IC_{50}$s were calculated (oligonucleotide concentration yielding 50% inhibition) and are shown in Table 12 along with $T_m$ data showing affinity of these oligonucleotides for their complement. Because of their extremely low $IC_{50}$s, both ISIS 10755 and ISIS 10754 are preferred. The oligonucleotides used in accordance with this invention may be conveniently and routinely made through the well-known technique of solid phase synthesis. (Martin, *Helv. Chim. Acta,* 1995, 78, 486–504.) Equipment for such synthesis is sold by several vendors including Applied Biosystems. Any other means for such synthesis may also be employed; the actual synthesis of the oligonucleotides is well within the talents of those skilled in the art.

TABLE 12

Antisense activity in T24 cells and $T_m$

| ISIS # | Modification | Tm (° C.) | $IC_{50}$ (nM) | SEQ ID NO: |
|---|---|---|---|---|
| 5132 | deoxy/P=S | 62.2 | 125 | 7 |
| 10755 | 2'-O—$CH_2CH_2OCH_3$/P=S | 76.1 | 20 | 7 |
| 10754 | 2'-O—$CH_2CH_2OCH_3$/ P = S/P=O | 77.5 | 20 | 7 |

Figure 8A:
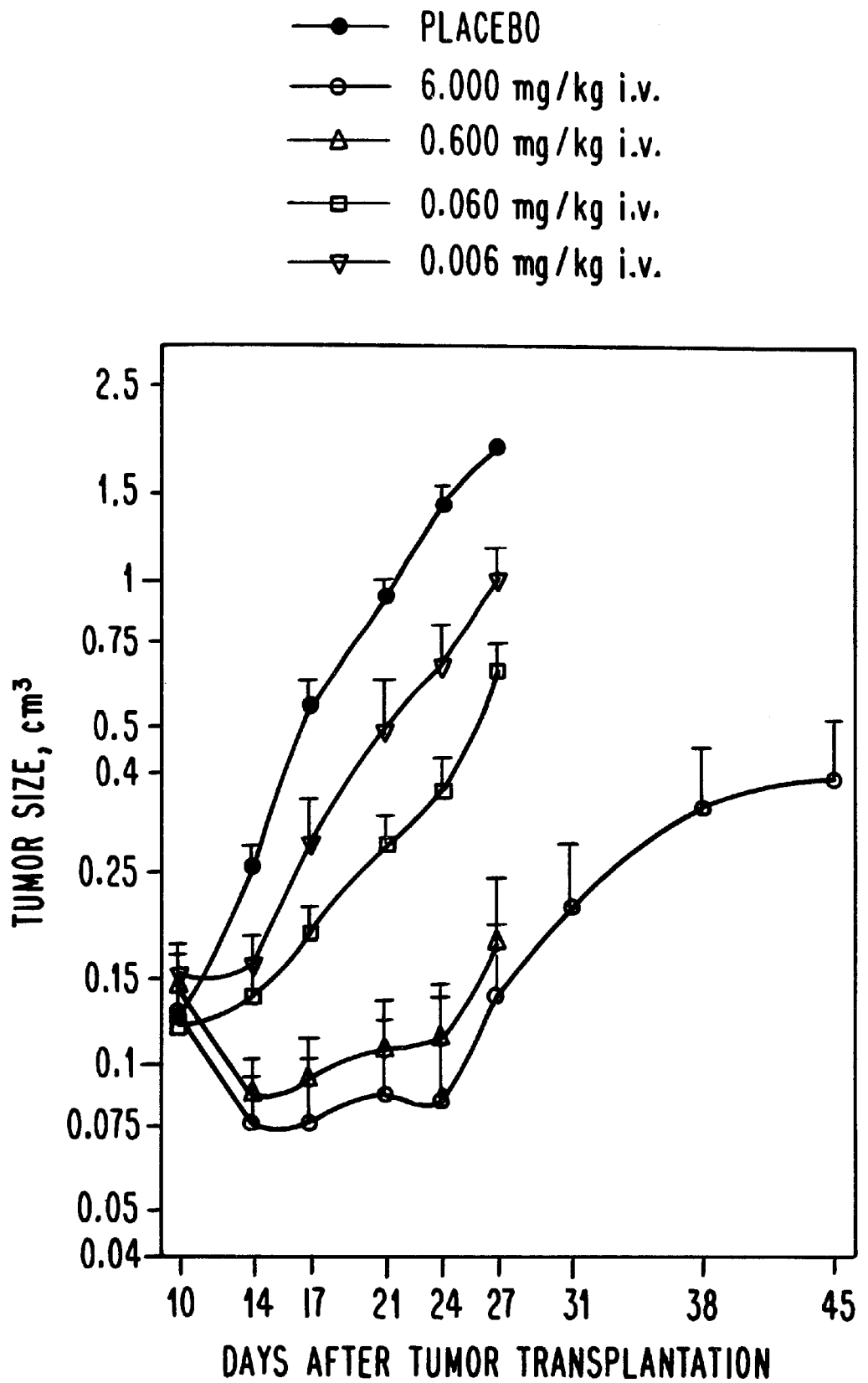
FIGS. 8a and 8b are line graphs showing the effect of ISIS 5132 (FIG. 6a) and CGP 69845, a 2'-methoxyethoxy (2'-O—CH$_2$—CH$_2$—O—CH$_3$) version of the same sequence (FIG. 6b), on the growth of A549 lung tumor xenografts in nude mice.
Figure 8B:
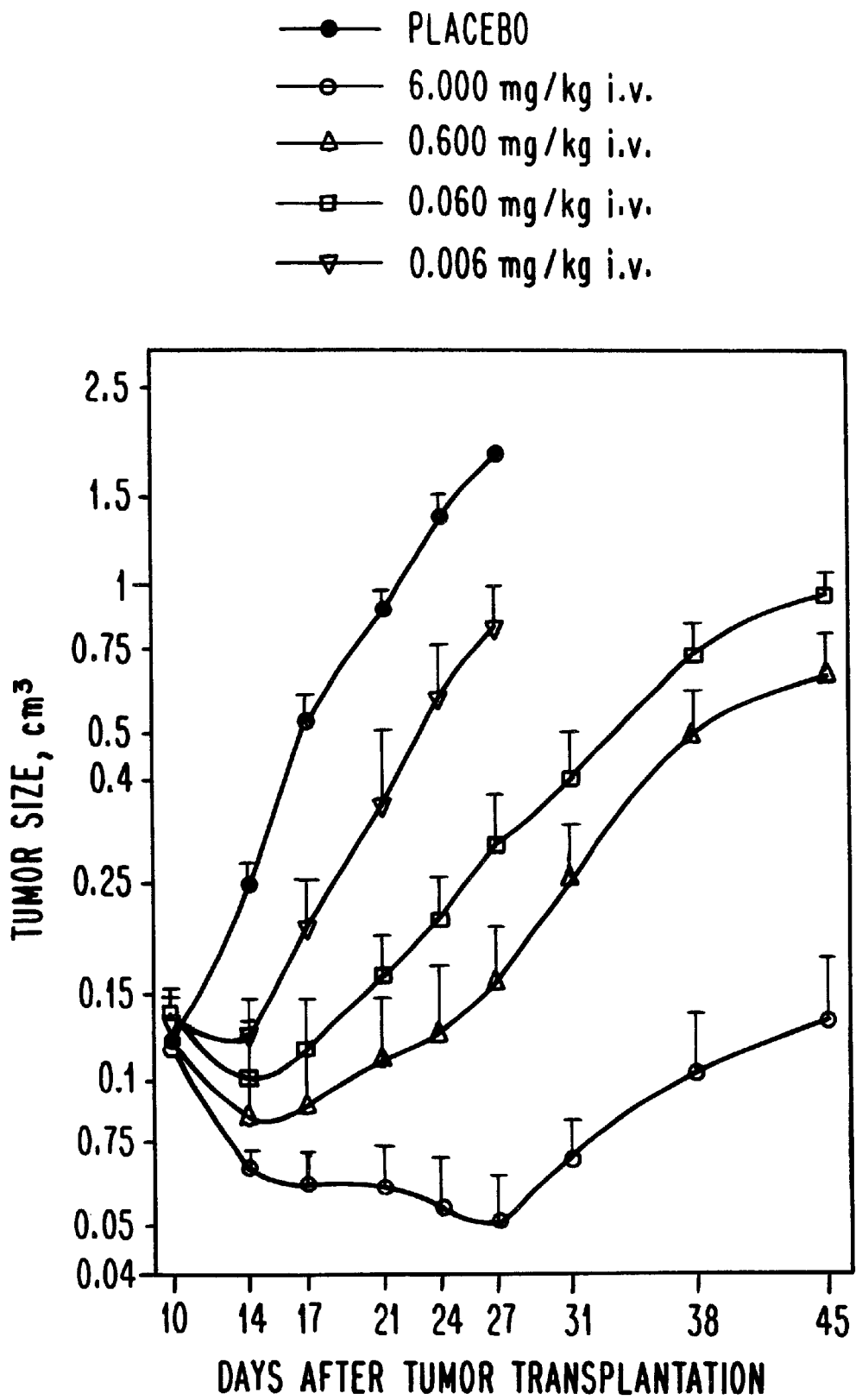

EXAMPLE 18
Effect of ISIS 5132 and CGP 69845 on A549 Human Lung Adenocarcinoma Tumors Subcutaneous human A549 lung adenocarcinoma xenografts were established in male Balb/c nude mice and treated with ISIS 5132 (SEQ ID NO: 7) or the methoxyethoxy (2'-O—$CH_2$—$CH_2$—O—$CH_3$) version of SEQ ID NO: 7 (CGP 69845), both administered daily by intravenous injection at doses ranging from 0.006 to 6.0 mg/kg. ISIS 5132 decreased tumor size at all doses in a dose-dependent manner, as shown in FIGS. 8a and 8b. The methoxyethoxy (2'-O—$CH_2$—$CH_2$—O—$CH_3$) oligonucleotide, CGP 69845, had similar effects to ISIS 5132 at the lower doses and even greater inhibitor effects than ISIS 5132 at a dose of 6.0 mg/kg.

EXAMPLE 19
A549 Xenogafts $5 \times 10^6$ A549 cells were implanted subcutaneously in the inner thigh of nude mice. Oligonucleotides (ISIS 5132 and CGP 69845, also known as ISIS 10754) suspended in saline were administered once daily by intravenous injection at doses ranging from 0.006 to 6.0 mg/kg. Resulting tumors were measured on days 9, 12, 17 and 21 and tumor volumes were calculated.

EXAMPLE 20
Northern Blot Analysis of Inhibition of c-raf mRNA Expression

The human urinary bladder cancer cell line T24 was obtained from the American Type Culture Collection (Rockville Md.). Cells were grown in McCoy's 5A medium with L-glutamine Gibco BRL, Gaithersburg Md.), supplemented with 10% heat-inactivated fetal calf serum and 50 U/mL each of penicillin and streptomycin. Cells were seeded on 100 mm plates. When they reached 70% confluency, they were treated with oligonucleotide. Plates were washed with 10 mL prewarmed PBS and 5 mL of OptiMEM reduced-serum medium containing 2.5 µL DOTMA. Oligonucleotide with lipofectin was then added to the desired concentration. After 4 hours of treatment, the medium was replaced with McCoy's medium. Cells were harvested 24 to 72 hours after oligonucleoride treatment and RNA was isolated using a standard CsCl purification method. Kingston, R. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, NY. Total RNA was isolated by centrifugation of cell lysates over a CsCl cushion. RNA samples were electrophoresed through 1.2% agarose-formaldehyde gels and transferred to hybridization membranes by capillary diffusion over a 12–14 hour period. The RNA was cross-linked to the membrane by exposure to UV light in a Stratalinker (Stratagene La Jolla, Calif.) and hybridized to random-primed $^{32}$P-labeled c-ra cDNA probe (obtained from ATCC) or G3PDH probe as a control RNA was quantitated using a Phosphorimager (Molecular Dynamics, Sunnyvale, Calif.).

EXAMPLE 21
Oligonucleotide Inhibition of Rev Gene Expression

The chimeric oligonucleotides used in this assay are shown in Table 13 below.

TABLE 13

Chimeric 2'-O-propyl deoxy P = S oligonucleotides
targeted to HIV rev gene
bold = 2'-O-propyl; s = P = S linkage;
o = P = O linkage

| OLIGO | SEQUENCE | SEQ ID NO: |
|---|---|---|
| 8907 | UoAoGoGoAoGoAsUsGsCsCsUsAsAoGoGoCoUoUoU | 20 |
| 8908 | GoCoUoAoUoGoUsCsGsAsCsAsCsCoCoAoAoUoUoC | 21 |
| 8909 | CoAoUoAoGoGoAsGSAsUsGsCsCsUoAoAoGoGoCoT | 22 |

Transfection and Luciferase assay: 3T3 cells were maintained in DMEM with glucose, L-glutamine, sodium pyruvate and 10% fetal bovine serum (GIBCO). For all experiments, cells were seeded the previous night at 75,000 cells/well in 6-well plates (Falcon). Transfections were performed using the standard $CaPO_4$ method. For each set of replicates, 15 µg/mL of pSG5/rev plasmid, 18 µg/mL pHIVenu-luc and 2 µg/mL of Rep 6 were precipitated and 200 µL of this was dripped on each well. The precipitate was allowed to incubate on cells for 7 hours at 37° C. The media was then aspirated, the cells washed once with PBS, and fresh complete media added for overnight incubation. Following incubation, the media was removed, cells washed with 2 mL of OPTIMEM (GIBCO) and 1 mL of OPTIMEM containing 2.5 µg/mL of Lipofectin (GIBCO-BRL) and the oligonucleotide added. The mixture was incubated for 4 hours at 37° C, at which point it was aspirated off the cells and complete media was added. Two hours after this treatment, 0.2 µM/mL of dexamethasone (Sigma) was added to all wells to allow induction of the MMTV promoter of pHIVenu-luc.

The Luciferase assay was performed 24 hours later, as follows: The wells were washed twice with PBS and the cells were harvested by scraping in 200 µL of lysis buffer (1% Triton, 25 mM glycylglycine, pH 7.8, 15 MM $MgSO_4$, 4 mM EGTA and 1 mM DTT)> The lysate was clarified by microfuging for 5 minutes at 11,500 rpm in the cold. 100 µL of the lysate was then combined in a microtiter plate with 50 µL of assay buffer (25 mm glycylglycine, pH 7.8, 15 MM $MgSO_4$, 4 mM EGTA, 15 mM potassium phosphate, pH 7.8, 1 mM DTT and 7.5 mM ATP). Luc detection was performed using a microtiter luminescent reader (Dynatech Laboratories). The reactions were started by injecting 50 µL of 1× luciferase solution (Sigma). The 1× solution was diluted in luciferin buffer (25 mM glycylglycine, pH 7.8, 15 mM $MgSO_4$, 4 mM EGTA and 4 mM DTT) prior to use from a 10 × stock (10 mM luciferin in 10 mM DTT). Samples were counted for 20 seconds. The kinetics of firefly luc light emission are characterized by a flash period lasting a few seconds followed by a period of lower light intensity emission lasting several minutes.

Rev and RRE RNA synthesis: pSG%-Rev contains the Rev gene adjacent to a T7 promoter. BglII linearized pSG5-Rev was used as a DNA template for transcription with T7 RNA polymerase. A template for the production of RRE RNA was produced by PCR. For RNA synthesis, DNA templates were used at 0.2 to 1.0 mg/mL, with 5 mM each of ATP, CTP and GTP, 0.5 mM of UTP, 10 mM of DTT, 40 mM of Tris-HCl, pH 7.5, 6 mM of $MgCl_2$, 4 mM of Spermidine, 500 U/mL of RNAsin at 20 U/µL, 2500 µCi/mL of α $^{32}$p UTP at 10 mCi/mL and 1000 U/mL of T7 RNA polymerase. The reaction was incubated for 1 hour at 37° C. The transcription reaction was terminated by adding formamide loading buffer and was run in a denaturing polyacrylamide gel containing 8 M urea. The RNA was eluted from the gel according to the procedure of Schwartz et al. (*Gene*, 1990, 88, 197).

EXAMPLE 22
Immunoassay for Antiviral Screening

NHDF cells were seeded in 96-well culture plates at a density of 15,000 cells/well in serum-free FGM. Established monolayers were pretreated with the oligonucleotide overnight in FGM prior to infection. After pretreatment, cells were rinsed thrice with fresh, prewarmed FGM, and virus in 100 µL of FGM/well was added to achieve an MOI of 0.05 PFU/cell. After 2 hours of incubation at 37° C., virus was removed and fresh medium (100 µL/well) containing the oligonucleotide was added. Medium was exchanged 2 days after infection with fresh medium containing the oligonucleotide, and 6 days after infection, the cells were fixed in absolute ethanol and dried in preparation for antibody staining. A modified protocol was used for some assays in which FGM was supplemented with low levels of FBS (0.2%), and the incubation period after infection was shortened from 6 days to 3 days. The shorter assay eliminated the need to exchange medium 2 days after infection. Both assays yielded comparable values for 50% effective concentrations (EC50s).

Fixed cells were blocked in a solution of PBS containing 2% bovine serum albumin (BSA), and mouse monoclonal antibody (1H10, supplied by Eisai Co., Ltd., Japan) was added in a 1:2000 dilution in PBS-1% BSA. The 1H10 antibody recognizes an abundant late HCMV polypeptide approximately 65 kDa in size. Detection of bound monoclonal antibody was facilitated with biotinylated goat anti-mouse immunoglobulin G abd streptavidin-coupled β-galactosidase (GIBCO-BRL, Gaithersburg, Md.). Chlorophenol red β-D-galactopyranoside was used as a substrate for β-galactosidase, and activity was determined by measuring the optical density at 575 nm of individual wells with a BioTex model EL312e microplate reader.

The oligonucleotides used in this assay are shown in Table 14 below.

TABLE 14

Inhibition of CMV replication by chimeric
2'-O-methyl p = S oligonucleotides
bold = 2'-O-methyl

| OLIGO | SEQUENCE | SEQ ID NO: |
|---|---|---|
| 4325 | GCG UUT GCT CTT CTT CUU GCG | 23 |
| 4326 | GCG UUU GCT CTT CTU CUU GCG | 24 |

EXAMPLE 23
Evaluation of Oligonucleotides 270 and 330 in an HCV H8Ad17 Protein Assay A Western blot assay employing affinity-purified human polyclonal anti-HCV serum and $^{125}$I-conjugated goat anti-human IgG was developed in place of ELISA assays previously used to evaluate effects of oligonucleotides on HCV core protein levels. Six-well plates were seeded with H8 cells at $3.5 \times 10^5$ cells/well. Cells were grown overnight. Cells were treated with oligonucleotide in Optimem containing 5 µg/mL lipofectin for 4 hours. Cells were fed with 2 mL H8 medium and allowed to recover overnight. To harvest cells, cells were washed once with 2 mL PBS, lysed in 100 µL Laemmli buffer and harvested by scraping. For electrophoresis, cell lysates were boiled, and 10–14 µL of cell lysate was loaded on each lane of a 16% polyacrylamide gel. After electrophoresing, proteins were transferred electrophoretically onto PVDF membrane. The membrane was blocked in PBS containing 2% goat serum and 0.3% Tween-20, and incubated overnight with primary antibody (human anti-core antibody 2243 and rabbit anti-G3PDH antibody). The membrane was washed 5x5 minutes in buffer, then incubated with secondary antibodies for 4–8 hours ($^{125}$I-conjugated goat anti-human, and $^{125}$I-conjugated goat anti-rabbit). The membrane was washed 5x5 minutes in buffer, sealed in plastic and exposed in a PhosphorImager cassette overnight. Bands were quantitated on the PhosphorImager (Molecular Dynamics, Sunnyvale Calif.), normalized to G3PDH expression levels, and results were plotted as a percentage of control untreated cells.

The oligonucleotides evaluated by this Western blot assay are shown in Table 15. In the sequences shown, capital letters represent base sequence, small letters (o or s) represent internucleoside linkage, either phosphodiester (P=O) or phosphorothioate (P=S), respectively. Bold=2'-O-propyl. *=2'-O-butylimidazole. +=2'-O-propylamine.

TABLE 15

| Oligo # | Sequence | SEQ ID NO: |
|---|---|---|
| 270A | GsTsAsCsCsAsCsAsAsGsGsC-sCsTsTsTsCsGsCsG | 25 |
| 270B | GsTsAsCsCsAsCsAsAsGsGsC-sCsTsTsTsCsGsCsG | 25 |
| 270C | GoToAoCoCoAoCoAoAoGoGoCoCoTo-ToToCoGoCoG<br>+ +   + + | 25 |
| 270D | GoToAoCoCoAoCoAoAoGoGoCoCoTo-ToToCoGoCoG | 25 |
| 330A | GsTsGsCsTsCsAsTsGsGsTsGsC-sAsCsGsGsTsCsT | 26 |
| 330B | GsTsGsCsTsCsAsTsGsGsTsGsC-sAsCsGsGsTsCsT | 26 |

TABLE 15-continued

| Oligo # | Sequence | SEQ ID NO: |
|---|---|---|
| * * | | * * |
| 330C | GoToGoCoToCoAoToGoGoToGo-CoAoCoGoGoToCoT<br>++ | 26 |
| 330D | GoToGoCoToCoAoToGoGoToGo-CoAoCoGoGoToCoT | 26 |

EXAMPLE 24

Synthesis of 2,6-Diamino-9-(2-O-octadecyl-β-D-ribofuranosyl)purine 2,6-Diamino-9-(β-D-ribofuranosyl)purine (50 g, 180 mmol) and sodium hydride (7 g) in DMF (1 L) were heated to boiling for 2 hr. Iodooctadecane (100 g) was added at 150° C. and the reaction mixture allowed to cool to RT. The reaction mixture was stirred for 11 days at RT. The solvent was evaporated and the residue purified by silica gel chromatography. The product was eluted with 5% MeOH/$CH_2C_2$. The appropriate fractions were evaporated to yield the product (11 g). $^1$H NMR (DMSO-$d_5$) δ0.84 (t, 3, $CH_2$); 1.22 (m, 32, O—$CH_2$—$CH_2$—$(CH_2)_{16}$); 1.86 (m, 2, O—$CH_2CH_2$); 3.25 (m, 2, O—$H_2$); 3.93 (d, 1, 4'H), 4.25 (m, 1, 3'H); 4.38 (t, 1, 2'H); 5.08 (d, 1, 3'-OH); 5.48 (t, 1, 5'-OH); 5.75 (s, 2, 6-$NH_2$); 5.84 (d, 1, 1'-H); 6.8 (s, 2, 2-$NH_2$); and 7.95 (s, 1, 8-H).

EXAMPLE 25

Synthesis of 2'-O-Octadecylguanosine 2, 6-Diamino-9-(2-O-octadecyl-β-D-ribofuranosyl)purine (10 g) in 0.1 M sodium phosphate buffer (50 mL, pH 7.4), 0.1 M tris buffer (1000 mL, pH 7.4) and DMSO (1000 mL) was treated with adenosine deaminase (1.5 g) at RT. At day 3, day 5 and day 7 an additional aliquot (500 mg, 880 mg and 200 mg, respectively) of adenosine deaminase was added. The reaction was stirred for a total of 9 day and purification by silica gel chromatography yielded the product (2 g). An analytical sample was recrystallized from MeOH $^1$H NMR (DMSO-$d_6$) δ0.84 (t, 3, $CH_3$), 1.22 [s, 32, O—$CH_2$—$CH_2$—$(CH_2)_{16}$], 5.07 (m, 2, 3'-OH and 5'-OH); 5.78 (d, 1, 1'-H); 6.43 (s, 2, $NH_2$), 7.97 (s, 1, 8-H) and 10.64 (s, 1, $NH_2$). Anal. Calcd. for $C_{28}H_{49}N_5O_5$: C, 62.80; H, 9.16; N, 12.95. Found: C, 62.54; H, 9.18; N, 12.95.

EXAMPLE 26

Synthesis of $N^2$-Isobutyryl-2'-O-octadecylguanosine

2'-O-Octadecylguanosine (1.9 g) in pyridine (150 mL) was cooled in an ice bath, and treated with trimethylsilyl chloride (2 g, 5 eq) and isobutyryl chloride (2 g, 5 eq). The reaction mixture was stirred for 4 hours, during which time it was allowed to warm to room temperature. The solution was cooled, water added (10 mL) and stirred for an additional 30 minutes. Concentrated ammonium hydroxide (10 mL) was added and the solution concentrated in vacuo. The residue was purified by silica gel chromatography (eluted with 3% MeOH/EtOAc) to yield 1.2 g of product. $^1$H NMR (DMSO-$d_6$) δ0.85 (t, 3, $CH_3$), 1.15 (m, 38, O—$CH_2CH_2$ $(CH_2)_{16}$, $CH(CH_3)_2$), 2.77 (m, 1, $CH(CH_3)_2$), 4.25 (m, 2, 2'-H and 3'-H); 5.08 (t, 1, 5'-OH), 5.12 (d, 1, 3'-OH), 5.87 (d, 1, 1'-H), 8.27 (s, 1, 8-H), 11.68 (s, 1, NH$_2$) and 12.08 (s, 1, NH$_2$). Anal. Calcd. for C$_{32}$H$_{55}$N$_5$O$_6$: C, 63.47; H, 9.09; N, 11.57. Found: C, 63.53; H, 9.20; N, 11.52. Prior to incorporating this product into an oligonucleotide, it was converted to N$^2$-Isobutyryl-5'-dimethoxytrityl-2'-O-octadecylguanosine and then to a phosphoramidite according to the procedures described in International Publication No. WO 94/02501, published Feb. 3, 1994.

EXAMPLE 27

Diagnostic Assay for the Detection of mRNA Overexpression

Oligonucleotides are radiolabeled after synthesis by $^{32}$p labeling at the 5' end with polynucleotide kinase. Sambrook et al. ["*Molecular Cloning. A Laboratory Manual,*" Cold Spring Harbor Laboratory Press, 1989, Volume 2, pg. 11.31–11.32]. Radiolabeled oligonucleotide is contacted with tissue or cell samples suspected of mRNA overexpression, such as a sample from a patient, under conditions in which specific hybridization can occur, and the sample is washed to remove unbound oligonucleotide. A similar control is maintained wherein the radiolabeled oligonucleotide is contacted with normal cell or tissue sample under conditions that allow specific hybridization, and the sample is washed to remove unbound oligonucleotide. Radioactivity remaining in the sample indicates bound oligonucleotide and is quantitated using a scintillation counter or other routine means. Comparison of the radioactivity remaining in the samples from normal and diseased cells indicates overexpression of the mRNA of interest.

Radiolabeled oligonucleotides of the invention are also useful in autoradiography. Tissue sections are treated with radiolabeled oligonucleotide and washed as described above, then exposed to photographic emulsion according to standard autoradiography procedures. A control with normal cell or tissue sample is also maintained. The emulsion, when developed, yields an image of silver grains over the regions overexpressing the mRNA, which is quantitated. The extent of mRNA overexpression is determined by comparison of the silver grains observed with normal and diseased cells.

Analogous assays for fluorescent detection of mRNA expression use oligonucleotides of the invention which are labeled with fluorescein or other fluorescent tags. Labeled DNA oligonucleotides are synthesized on an automated DNA synthesizer (Applied Biosystems model 380B) using standard phosphoramidite chemistry with oxidation by iodine. δ-cyanoethyldiisopropyl phosphoramidites are purchased from Applied Biosystems (Foster City, Calif.). Fluorescein-labeled amidites are purchased from Glen Research (Sterling, Va.). Incubation of oligonucleotide and biological sample is carried out as described for radiolabeled oligonucleotides except that instead of a scintillation counter, a fluorescence microscope is used to detect the fluorescence. Comparison of the fluorescence observed in samples from normal and diseased cells enables detection of mRNA overexpression.

EXAMPLE 28

Detection of Abnormal mRNA Expression

Tissue or cell samples suspected of expressing abnormal mRNA are incubated with a first $^{32}$p or fluorescein-labeled oligonucleotide which is targeted to the wild-type (normal) mRNA. An identical sample of cells or tissues is incubated with a second labeled oligonucleotide which is targeted to the abnormal mRNA, under conditions in which specific hybridization can occur, and the sample is washed to remove unbound oligonucleotide. Label remaining in the sample indicates bound oligonucleotide and can be quantitated using a scintillation counter, fluorimeter, or other routine means. The presence of abnormal mRNA is indicated if binding is observed in the case of the second but not the first sample.

Double labeling can also be used with the oligonucleotides and methods of the invention to specifically detect expression of abnormal mRNA. A single tissue sample is incubated with a first $^{32}$P-labeled oligonucleotide which is targeted to wild-type mRNA, and a second fluorescein-labeled oligonucleotide which is targeted to the abnormal mRNA, under conditions in which specific hybridization can occur. The sample is washed to remove unbound oligonucleotide and the labels are detected by scintillation counting and fluorimetry. The presence of abnormal mRNA is indicated if the sample does not bind the $^{32}$P-labeled oligonucleotide (i.e., is not radioactive) but does retain the fluorescent label (i.e., is fluorescent).

EXAMPLE 29

Plasma Uptake and Tissue Distribution of Oligonucleotides in Mice

The following oligonucleotides were prepared:

U$s$G$s$C$s$A$s$T$s$C$s$C$s$C$s$C$s$C$s$A$s$G$s$G$s$C$s$C$s$A$s$C$s$C$s$A$s$T, SEQ ID NO:27

U$s$G$s$C$s$A$s$T$s$C$s$C$s$C$s$C$s$A$s$G$s$G$s$C$s$C$s$A$s$C$s$C$s$A$s$T, SEQ ID NO:27

U$s$G$s$C$s$A$s$T$s$C$s$C$CCCAGG$C$s$C$s$A$s$C$s$C$s$A$s$T, SEQ ID NO:27 wherein bold type indicated a 2'-O-propyl substituent, "s" indicates a phosphorothioate linkage and the absence of "s" indicates a phosphodiester linkage in the respective oligonucleotides. The first oligonucleotide is identified as ISIS 3082, the second as ISIS 9045, and the third as ISIS 9046 in FIGS. 9, 10, 11 and 12. The oligonucleotides were tritiated as per the procedure of Graham et al., *Nuc. Acids Res.*, 1993, 16, 3737–3743.

Animals and Experimental Procedure: For each oligonucleotide studied, twenty male Balb/c mice (Charles River), weighing about 25 g, were randomly assigned into one of four treatment groups. Following a one-week acclimation, mice received a single tail vein injection of $^3$H-radiolabeled oligonucleotide (approximately 750 nmoles/kg; ranging from 124–170 μCi/kg) administered in phosphate buffered saline, pH 7.0. The concentration of oligonucleotide in the dosing solution was approximately 60 μM. One retro-orbital bleed (at either 0.25, 0.5, 2, or 4 hours post-dose) and a terminal bleed (either 1, 3, 8 or 24 hours post-dose) was collected from each group. The terminal bleed was collected by cardiac puncture following ketamine/xylazine anesthesia. An aliquot of each blood sample was reserved for radioactivity determination and the remaining blood was transferred to an EDTA-coated collection tube and centrifuged to obtain plasma. Urine and feces were collected at intervals (0–4, 4–8 and 8–24 hours) from the group terminated at 24 hours.

At termination, the liver, kidneys, spleen, lungs, heart, brain, sample of skeletal muscle, portion of the small intestine, sample of skin, pancreas, bone (both femurs containing marrow) and two lymph nodes were collected from each mouse and weighed. Feces were weighed, then homogenized 1:1 with distilled water using a Brinkmann Polytron homogenizer (Westbury, N.Y.). Plasma, tissues, urine and feces homogenate were divided for the analysis of radioactivity by combustion and for determination of intact oligonucleotide content. All samples were immediately frozen on dry ice after collection and stored at −80° C. until analysis.

Analysis of Radioactivity in Plasma, Tissue, and Excreta: Plasma and urine samples were weighed directly into scintillation vials and analyzed directly by liquid scintillation counting after the addition of 15 mL of BetaBlend (ICN Biomedicals, Costa Mesa, Calif.). All other samples (tissues, blood and homogenized feces) were weighed into combustion boats and oxidized in a Biological Materials Oxidizer (Model OX-100; R. J. Harvey Instrument Corp., Hillsdale, N.J.). The $^3H_2O$ was collected in 20 mL of cocktail, composed of 15 mL of BetaBlend and 5 mL of Harvey Tritium Cocktail (R. J. Harvey Instrument Corp., Hillsdale, N.J.). The combustion efficiency was determined daily by combustion of samples spiked with a solution of $^3H$-mannitol and ranged between 73.9–88.3%. Liquid scintillation counting was performed using a Beckman LS 9800 or LS 6500 Liquid Scintillation System (Beckman Instruments, Fullerton, Calif.). Samples were counted for 10 minutes with automatic quench correction. Disintegration per minute values were corrected for the efficiency of the combustion process.

Analysis of Data: Radioactivity in samples was expressed as disintegrations per minute per gram of sample. These values were divided by the specific activity of the radiolabel to express the data in nanomole-equivalents of total oligonucleotide per gram of sample, then converted to percent of dose administered per organ or tissue. Assuming a tissue density of 1 g/mL, the nmole/g data were converted to a total $\mu$M concentration. To calculate the concentration of intact oligonucleotide in plasma, liver or kidney at each time point, the mean total $\mu$M concentrations were divided by the percent of intact oligonucleotide in the dosing solution (82–97%), then multiplied by the mean percentage of intact oligonucleotide at each time point as determined by CGE or HPLC. This data was then used for the calculation of tissue half-lives by linear regression and to compare the plasma pharmacokinetics of the different modified oligonucleotides. The pharmacokinetic parameters were determined using PCNONLIN 4.0 (Statistical Consultants, Inc., Apex, N.C.). After examination of the data, a one-compartment bolus input, first order output model (library model 1) was selected for use.

Figure 9:
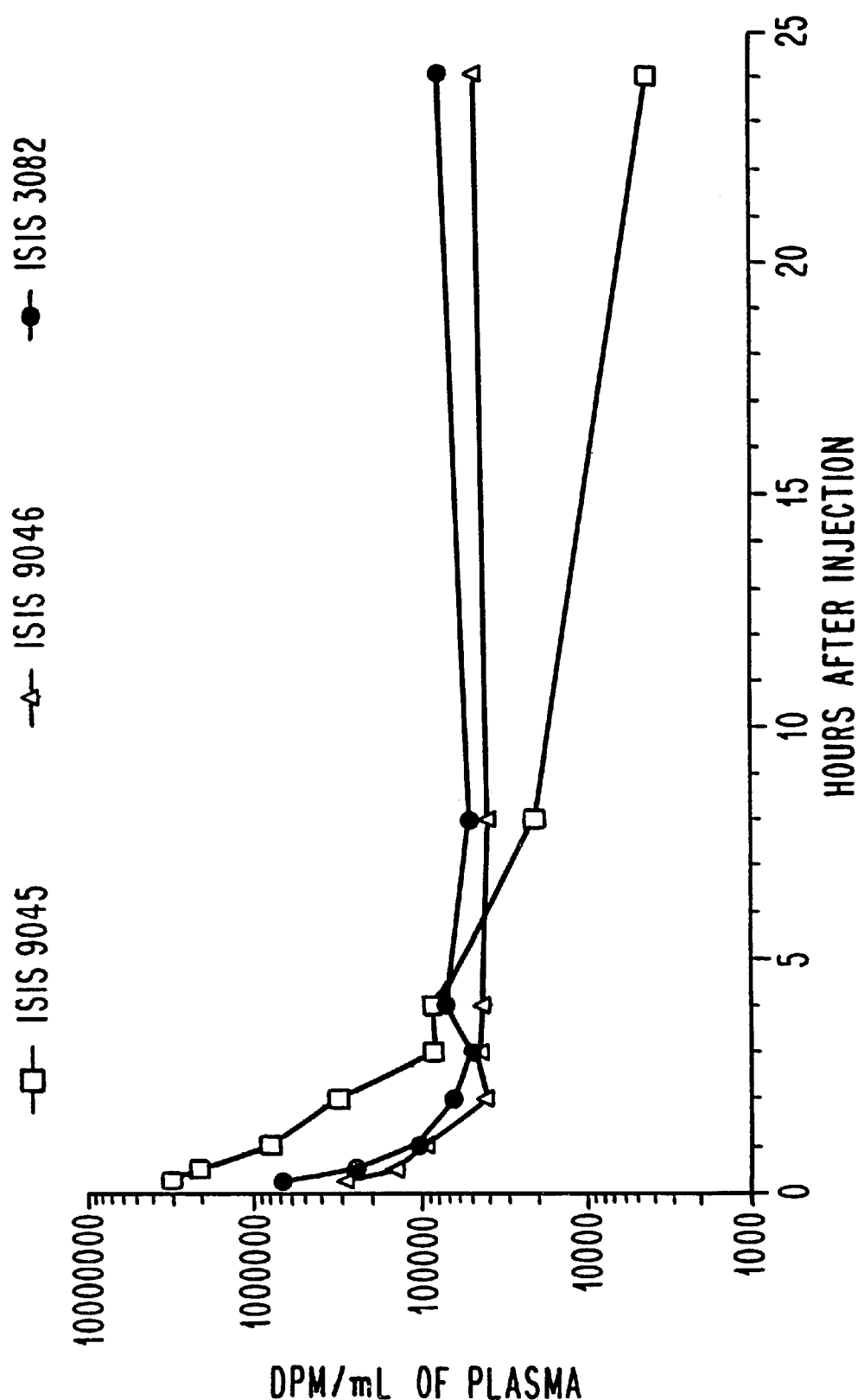
FIG. 9 is a line graph showing mouse plasma 9 concentrations of a control compound and two compounds of the invention. The plasma concentration is plotted versus time.
Figure 10:
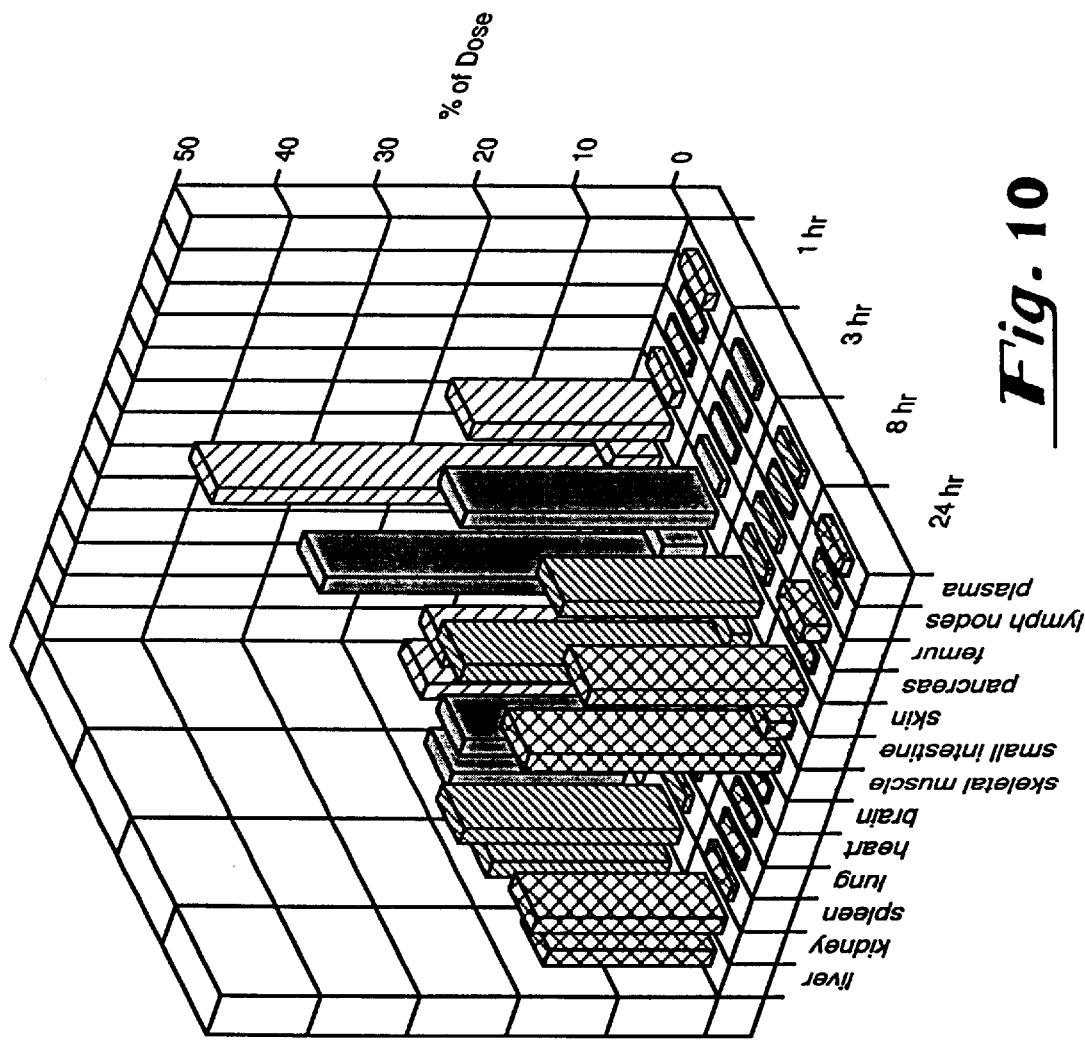
FIG. 10 is a three dimensional bar graph showing distribution of a control compound among various tissues in mouse. Specific tissues are shown on one axis, time on a second axis and percent of dose on the third axis. The compound was delivered by intravenous injection.
Figure 11:
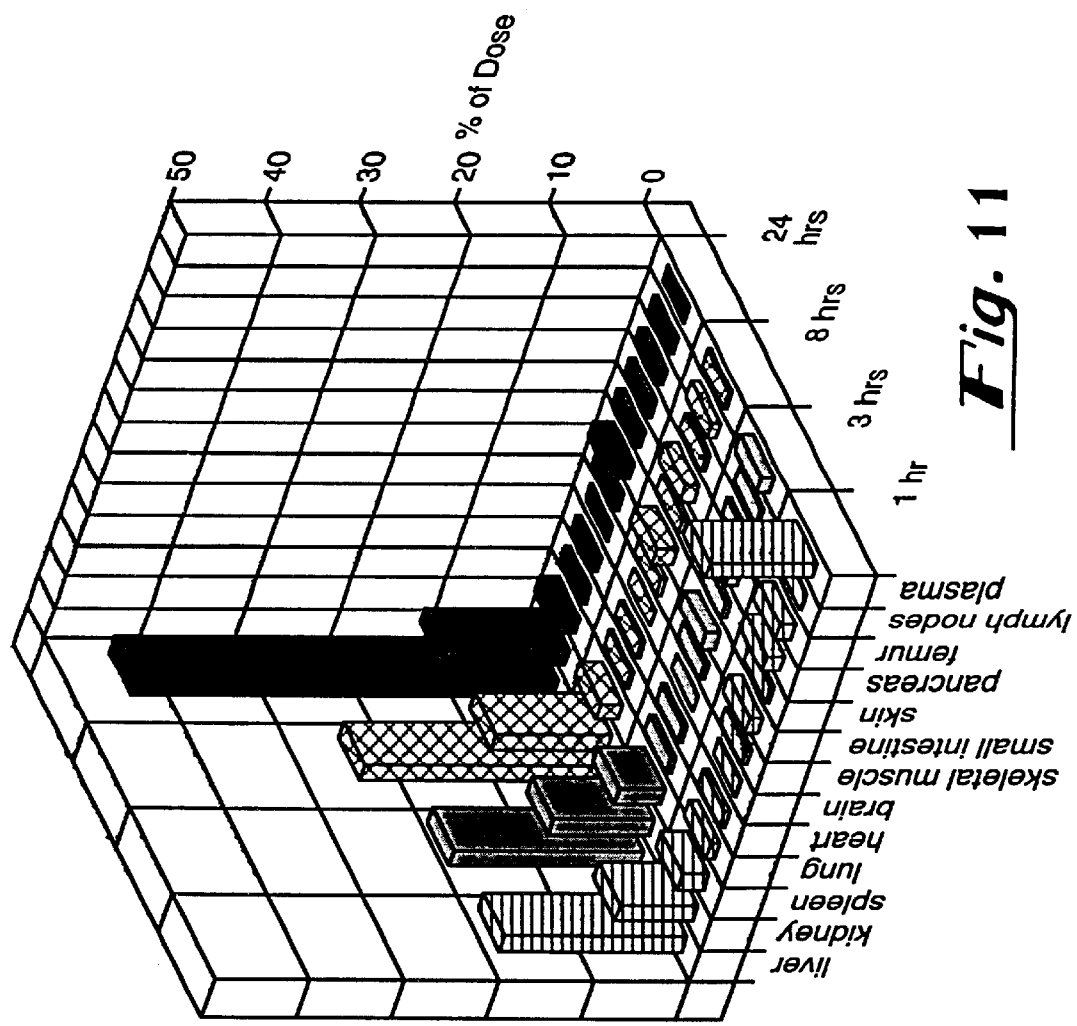
FIG. 11 is a three dimensional bar graph showing distribution of a compound of the invention among various tissues in mouse. Specific tissues are shown on one axis, time on a second axis and percent of dose on the third axis. The compound was delivered by intravenous injection.
Figure 12:
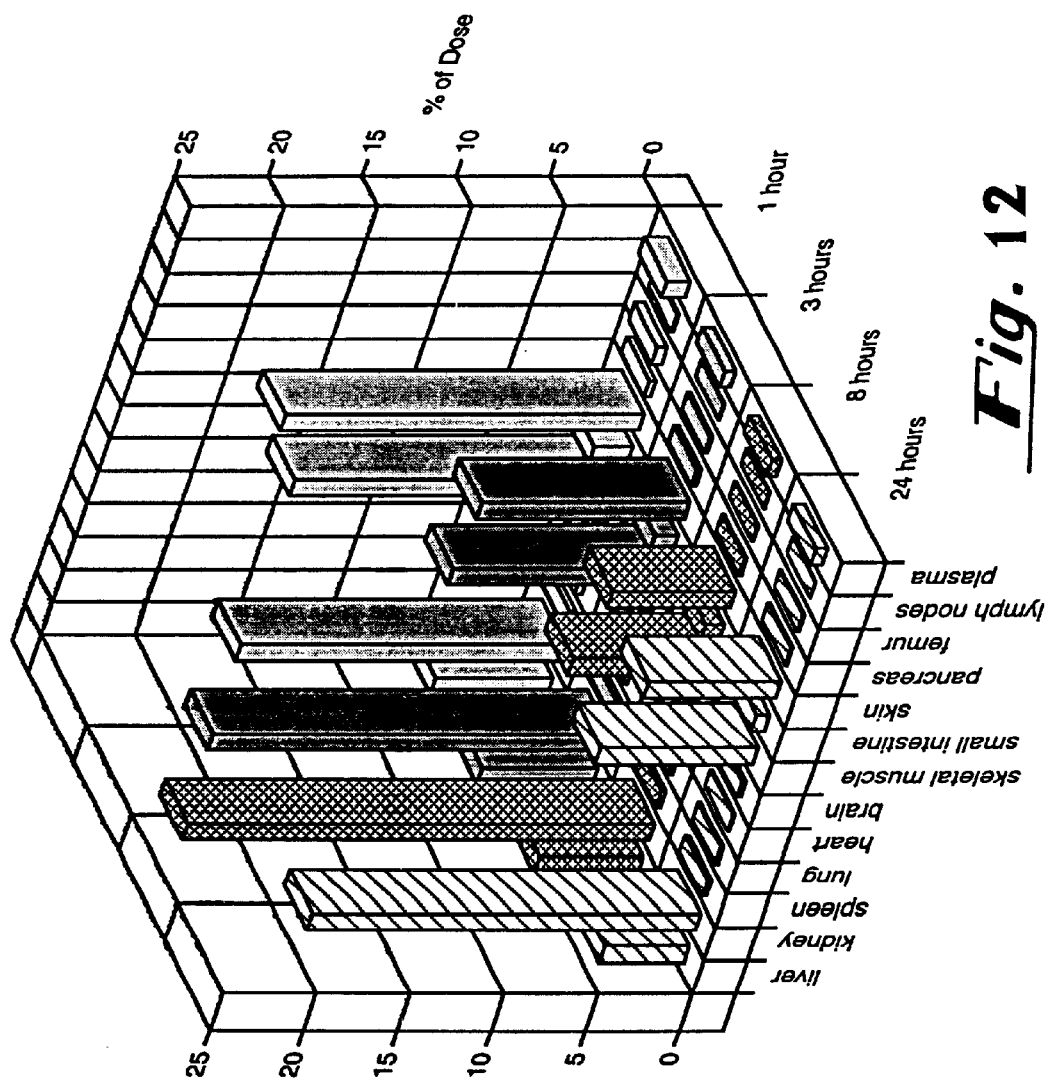
FIG. 12 is a three dimensional bar graph showing distribution of a further compound of the invention among various tissues in mouse. Specific tissues are shown on one axis, time on a second axis and percent of dose on the third axis. The compound was delivered by intravenous injection.

The result of the animal plasma uptake and tissue distribution tests are illustrated graphically in FIGS. 9, 10, 11 and 12. As is seen in FIG. 9, plasma concentration of each of the test oligonucleotides decrease from the initial injection levels to lower levels over the twenty-four hour test period. Plasma concentrations of the oligonucleotides of the invention were maintained at levels equivalent to those of the non-conjugate bearing phosphorothioate. All of the test compounds were taken up from the plasma to tissues as is shown in FIGS. 10, 11 and 12. The compounds of the invention had different distribution between the various tissues. FIG. 10 shows the distribution pattern for the control oligonucleotide, identified as ISIS 3082, a phosphorothioate oligonucleotide. FIG. 11 shows the distribution pattern for a first compound of the invention, an oligonucleotide, identified as ISIS 9045, having a 2'-substituent at each nucleoside. FIG. 12 shows the distribution pattern for a further compound of the invention, a "gapped" oligonucleotide, identified as ISIS 9046, having a 2'-substituent and phosphodiester linkages at each nucleoside at "flanking" sections of the oligonucleotide and 2'-deoxy, phosphorothioate nucleosides in a central or gap region.

EXAMPLE 30

2,2'-Anhydro[1-(β-D-arabinofuranosyl)-5-methyluridine]

5-Methyluridine (ribosylthymine, commercially available through Yamasa, Choshi, Japan) (72.0 g, 0.279 M), diphenyl-carbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

EXAMPLE 31

2'-O-Methoxyethyl-5-methyluridine 2,2'-Anhydro-5-methyluridine (195 g, 0.81 M), tris (2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/ MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

EXAMPLE 32

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

EXAMPLE 33

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tic sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporate to give 122 g of residue (approx. 90% product). The residue was purified on a 3.5 kg silica gel column and eluted using EtOAc/Hexane(4:1). Pure product fractions were evaporated to yield 96 g (84%). An additional 1.5 g was recovered from later fractions.

EXAMPLE 34

3'-O-Acetyl-2'-O-methoxyethyl-5'-O-dimethoxytrityl-5-methyl-4-triazoleuridine A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

EXAMPLE 35

2'-O-Methoxyethyl-5'-O-dimethoxytrityl-5-methylcytidine

A solution of 3'-O-acetyl-2'-O-methoxyethyl-5'-O-dimethoxy-trityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

EXAMPLE 36

$N^4$-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/Hexane (1:1) containing 0.5% $Et_3NH$ as the eluting solvent. The pure product fractions were evaporated to give 90 g (90%) of the title compound.

EXAMPLE 37

$N^4$-Benzoyl-2'-O-methoxyethyl-5'-O-dimethoxytrityl-5-methylcytidine-3'-amidite $N^4$-Benzoyl-2'-O-methoxyethyl-5'-O-dimethoxytrityl-5-methyl-cytidine (74 g, 0.10 M) was dissolved in $CH_2Cl_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc/Hexane (3:1) as the eluting solvent. The pure fractions were combined to give 90.6 g (87%) of the title compound.

---

What is claimed is:

1. An oligonucleotide specifically hybridizable with DNA or RNA said oligonucleotide comprising a linear sequence of covalently-bound nucleoside units, wherein:
said sequence comprises a first nucleoside subsequence having adjacent 2'-O—$CH_2$—$CH_2$—O—$CH_3$ sugar moieties and a second nucleoside subsequence having adjacent 2'-deoxy sugar moieties, wherein:
said nucleoside units of said first and second subsequences are covalently-bound by phosphorothioate linkages; or
said nucleoside units of said first subsequence are covalently-bound by phosphodiester linkages and said nucleoside units of said second subsequence are covalently-bound by phophorothioate linkages; or
said nucleoside units of said first subsequence are covalently-bound by phosphorothioate linkages and said nucleoside units of said second subsequence are covalently-bound by phosphodiester linkages.

2. The oligonucleotide of claim 1 wherein said nucleoside units of said first and second subsequences are covalently-bound by phosphorothioate linkages.

3. The oligonucleotide of claim 1 wherein said nucleoside units of said first subsequence are covalently-bound by phosphodiester linkages and said nucleoside units of said second subsequence are covalently-bound by phosphorothioate linkages.

4. The oligonucleotide of claim 1 wherein said nucleoside units of said first subsequence are covalently-bound by phosphorothioate linkages and said nucleoside units of said second subsequence are covalently-bound by phosphodiester linkages.

5. The oligonucleotide of claim 1 wherein said second subsequence comprises at least three nucleoside units.

6. The oligonucleotide of claim 1 wherein said second subsequence comprises at least five nucleoside units.

7. The oligonucleotide of claim 1 having 5 to 50 nucleoside units.

8. An oligonucleotide specifically hybridizable with DNA or RNA said oligonucleotide comprising a linear sequence of covalently-bound nucleoside units, wherein:

said sequence comprises a first nucleoside subsequence having adjacent 2'-$OCH_2$—$CH_2$—O—$CH_3$ sugar moieties, a second nucleoside subsequence having adjacent 2'-deoxy sugar moieties, and a third nucleoside subsequence having adjacent 2'-O—$CH_2$—$CH_2$—O—$CH_3$ sugar moieties, wherein said second subsequence is positioned between said first and third subsequences; and the nucleoside units within said first, second, and third subsequences are covalently-bound by phosphodiester or phophorothioate linkages.

9. The oligonucleotide of claim 8 wherein said nucleoside units of said first, second and third subsequences are covalently-bound by phosphorothioate linkages.

10. The oligonucleotide of claim 8 wherein said nucleoside units of said first and thir subsequences are covalently-bound by phosphodiester linkages and said nucleoside units of said second subsequence are covalently-bound by phosphorothioate linkages.

11. The oligonucleotide of claim 8 wherein said nucleoside units of said first and third subsequences are covalently-bound by phosphorothioate linkages and said nucleoside units of said second subsequence are covalently-bound by phosphodiester linkages.

12. The oligonucleotide of claim 8 wherein said second subsequence comprises at least three nucleoside units.

13. The oligonucleotide of claim 8 wherein said second subsequence comprises at least five nucleoside units.

14. The oligonucleotide of claim 8 having 5 to 50 nucleoside units.

* * * * *

SEQUENCE LISTING

<160> NUMBER OF SEQ ID NOS: 32

<210> SEQ ID NO 1
<211> LENGTH: 17
<212> TYPE: DNA
<213> ORGANISM: Artificial Sequence
<220> FEATURE:
<223> OTHER INFORMATION: Novel Sequence

<400> SEQUENCE: 1
ccacaccgac ggcgccc

```
<210> SEQ ID NO 2
<211> LENGTH: 20
<212> TYPE: DNA
<213> ORGANISM: Artificial Sequence
<220> FEATURE:
<223> OTHER INFORMATION: Novel Sequence

<400> SEQUENCE: 2
cttatattcc gtcatcgctc                                                     20

<210> SEQ ID NO 3
<211> LENGTH: 20
<212> TYPE: DNA
<213> ORGANISM: Artificial Sequence
<220> FEATURE:
<223> OTHER INFORMATION: Novel Sequence

<400> SEQUENCE: 3
tccgtcatcg ctcctcaggg                                                     20

<210> SEQ ID NO 4
<211> LENGTH: 20
<212> TYPE: DNA
<213> ORGANISM: Artificial Sequence
<220> FEATURE:
<223> OTHER INFORMATION: Novel Sequence

<400> SEQUENCE: 4
aaaacgtcag ccatggtccc                                                     20

<210> SEQ ID NO 5
<211> LENGTH: 18
<212> TYPE: DNA
<213> ORGANISM: Artificial Sequence
<220> FEATURE:
<223> OTHER INFORMATION: Novel Sequence

<400> SEQUENCE: 5
ttctcgctgg tgagtttc                                                       18

<210> SEQ ID NO 6
<211> LENGTH: 17
<212> TYPE: DNA
<213> ORGANISM: Artificial Sequence
<220> FEATURE:
<223> OTHER INFORMATION: Novel Sequence

<400> SEQUENCE: 6
tctcgctggt gagtttc                                                        17

<210> SEQ ID NO 7
<211> LENGTH: 20
<212> TYPE: DNA
<213> ORGANISM: Artificial Sequence
<220> FEATURE:
<223> OTHER INFORMATION: Novel Sequence

<400> SEQUENCE: 7
tcccgcctgt gacatgcatt                                                     20

<210> SEQ ID NO 8
<211> LENGTH: 20
<212> TYPE: DNA
<213> ORGANISM: Artificial Sequence
<220> FEATURE:
<223> OTHER INFORMATION: Novel Sequence
```

<400> SEQUENCE: 8
tcctcctccc cgcggcgggt                                        20

<210> SEQ ID NO 9
<211> LENGTH: 20
<212> TYPE: DNA
<213> ORGANISM: Artificial Sequence
<220> FEATURE:
<223> OTHER INFORMATION: Novel Sequence

<400> SEQUENCE: 9
ctcgcccgct cctcctcccc                                        20

<210> SEQ ID NO 10
<211> LENGTH: 20
<212> TYPE: DNA
<213> ORGANISM: Artificial Sequence
<220> FEATURE:
<223> OTHER INFORMATION: Novel Sequence

<400> SEQUENCE: 10
ttctcgcccg ctcctcctcc                                        20

<210> SEQ ID NO 11
<211> LENGTH: 20
<212> TYPE: DNA
<213> ORGANISM: Artificial Sequence
<220> FEATURE:
<223> OTHER INFORMATION: Novel Sequence

<400> SEQUENCE: 11
ttctcgcccg ctcctcctcc                                        20

<210> SEQ ID NO 12
<211> LENGTH: 20
<212> TYPE: DNA
<213> ORGANISM: Artificial Sequence
<220> FEATURE:
<223> OTHER INFORMATION: Novel Sequence

<400> SEQUENCE: 12
ctggcttctc ctcctcccct                                        20

<210> SEQ ID NO 13
<211> LENGTH: 20
<212> TYPE: DNA
<213> ORGANISM: Artificial Sequence
<220> FEATURE:
<223> OTHER INFORMATION: Novel Sequence

<400> SEQUENCE: 13
cctgctggct tctcctcctc                                        20

<210> SEQ ID NO 14
<211> LENGTH: 20
<212> TYPE: DNA
<213> ORGANISM: Artificial Sequence
<220> FEATURE:
<223> OTHER INFORMATION: Novel Sequence

<400> SEQUENCE: 14
tctggcgctg csccsctctc                                        20

<210> SEQ ID NO 15

```
<211> LENGTH: 47
<212> TYPE: DNA
<213> ORGANISM: Artificial Sequence
<220> FEATURE:
<223> OTHER INFORMATION: Novel Sequence

<400> SEQUENCE: 15
acattatgct agcttttga gtaaacttgt ggggcaggag accctgt                47

<210> SEQ ID NO 16
<211> LENGTH: 29
<212> TYPE: DNA
<213> ORGANISM: Artificial Sequence
<220> FEATURE:
<223> OTHER INFORMATION: Novel Sequence

<400> SEQUENCE: 16
gagatctgaa gcttctggat ggtcagcgc                                   29

<210> SEQ ID NO 17
<211> LENGTH: 35
<212> TYPE: DNA
<213> ORGANISM: Artificial Sequence
<220> FEATURE:
<223> OTHER INFORMATION: Novel Sequence

<400> SEQUENCE: 17
gagatctgaa gcttgaagac gccaaaaaca taaag                            35

<210> SEQ ID NO 18
<211> LENGTH: 33
<212> TYPE: DNA
<213> ORGANISM: Artificial Sequence
<220> FEATURE:
<223> OTHER INFORMATION: Novel Sequence

<400> SEQUENCE: 18
acgcatctgg cgcgccgata ccgtcgacct cga                              33

<210> SEQ ID NO 19
<211> LENGTH: 20
<212> TYPE: DNA
<213> ORGANISM: Artificial Sequence
<220> FEATURE:
<223> OTHER INFORMATION: Novel Sequence

<400> SEQUENCE: 19
cgggaggcgg tcacattcgg                                             20

<210> SEQ ID NO 20
<211> LENGTH: 20
<212> TYPE: RNA
<213> ORGANISM: Artificial Sequence
<220> FEATURE:
<223> OTHER INFORMATION: Novel Sequence

<400> SEQUENCE: 20
uaggagaugc cuaaggcuuu                                             20

<210> SEQ ID NO 21
<211> LENGTH: 20
<212> TYPE: RNA
<213> ORGANISM: Artificial Sequence
<220> FEATURE:
<223> OTHER INFORMATION: Novel Sequence

<400> SEQUENCE: 21
```

-continued gcuaugucga cacccaauuc                                              20

<210> SEQ ID NO 22
<211> LENGTH: 20
<212> TYPE: DNA
<213> ORGANISM: Artificial Sequence
<220> FEATURE:
<223> OTHER INFORMATION: Novel Sequence

<400> SEQUENCE: 22
cauaggagau gccuaaggct                                              20

<210> SEQ ID NO 23
<211> LENGTH: 21
<212> TYPE: DNA
<213> ORGANISM: Artificial Sequence
<220> FEATURE:
<223> OTHER INFORMATION: Novel Sequence

<400> SEQUENCE: 23
gcguutgctc ttcttcuugc g                                            21

<210> SEQ ID NO 24
<211> LENGTH: 21
<212> TYPE: DNA
<213> ORGANISM: Artificial Sequence
<220> FEATURE:
<223> OTHER INFORMATION: Novel Sequence

<400> SEQUENCE: 24
gcguuugctc ttctucuugc g                                            21

<210> SEQ ID NO 25
<211> LENGTH: 20
<212> TYPE: DNA
<213> ORGANISM: Artificial Sequence
<220> FEATURE:
<223> OTHER INFORMATION: Novel Sequence

<400> SEQUENCE: 25
gtaccacaag gcctttcgcg                                              20

<210> SEQ ID NO 26
<211> LENGTH: 20
<212> TYPE: DNA
<213> ORGANISM: Artificial Sequence
<220> FEATURE:
<223> OTHER INFORMATION: Novel Sequence

<400> SEQUENCE: 26
gtgctcatgg tgcacggtct                                              20

<210> SEQ ID NO 27
<211> LENGTH: 20
<212> TYPE: DNA
<213> ORGANISM: Artificial Sequence
<220> FEATURE:
<223> OTHER INFORMATION: Novel Sequence

<400> SEQUENCE: 27
ugcatccccc aggccaccat                                              20

<210> SEQ ID NO 28
<211> LENGTH: 16
<212> TYPE: DNA

```
<213> ORGANISM: Artificial Sequence
<220> FEATURE:
<223> OTHER INFORMATION: Novel Sequence

<400> SEQUENCE: 28
gcgttttttt tttgcg                                                      16

<210> SEQ ID NO 29
<211> LENGTH: 19
<212> TYPE: DNA
<213> ORGANISM: Artificial Sequence
<220> FEATURE:
<223> OTHER INFORMATION: Novel Sequence

<400> SEQUENCE: 29
cgcaaaaaaa aaaaaacgc                                                   19

<210> SEQ ID NO 30
<211> LENGTH: 20
<212> TYPE: DNA
<213> ORGANISM: Artificial Sequence
<220> FEATURE:
<223> OTHER INFORMATION: Novel Sequence

<400> SEQUENCE: 30
gttctcgctg gtgagtttca                                                  20

<210> SEQ ID NO 31
<211> LENGTH: 20
<212> TYPE: DNA
<213> ORGANISM: Artificial Sequence
<220> FEATURE:
<223> OTHER INFORMATION: Novel Sequence

<400> SEQUENCE: 31
ccccaaccac ctcttgctcc                                                  20

<210> SEQ ID NO 32
<211> LENGTH: 20
<212> TYPE: DNA
<213> ORGANISM: Artificial Sequence
<220> FEATURE:
<223> OTHER INFORMATION: Novel Sequence

<400> SEQUENCE: 32
gagaccctga acagttgatc                                                  20
```